United States Patent
Martens et al.

(10) Patent No.: US 11,846,684 B2
(45) Date of Patent: *Dec. 19, 2023

(54) MAGNETIC FIELD PROBE FOR DETERMINING A DISPOSITION OF AN IMPLANTABLE MAGNETIC MARKER

(71) Applicant: SIRIUS MEDICAL SYSTEMS B.V., Eindhoven (NL)

(72) Inventors: Hubert Cécile Francois Martens, Eindhoven (NL); Bram Schermers, Eindhoven (NL); Takeshi Kaneko, Eindhoven (NL); Jeroen Hendrik Franken, Eindhoven (NL)

(73) Assignee: SIRIUS MEDICAL SYSTEMS B.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/965,223

(22) Filed: Oct. 13, 2022

(65) Prior Publication Data
US 2023/0031115 A1  Feb. 2, 2023

Related U.S. Application Data

(63) Continuation of application No. 17/322,401, filed on May 17, 2021, now Pat. No. 11,513,168, which is a (Continued)

(30) Foreign Application Priority Data

Nov. 29, 2018  (NL) .................................... 2022093

(51) Int. Cl.
*G01R 33/00* (2006.01)
*A61B 5/06* (2006.01)
*G01R 33/02* (2006.01)

(52) U.S. Cl.
CPC .......... *G01R 33/0005* (2013.01); *A61B 5/062* (2013.01); *G01R 33/02* (2013.01); *A61B 2562/0223* (2013.01)

(58) Field of Classification Search
CPC .... G01R 33/0005; G01R 33/02; A61B 5/062; A61B 2562/0223
See application file for complete search history.

(56) References Cited

U.S. PATENT DOCUMENTS

| 7,561,051 B1 | 7/2009 | Kynor et al. | |
| 2004/0097803 A1* | 5/2004 | Panescu | A61B 5/06 600/424 |

(Continued)

FOREIGN PATENT DOCUMENTS

WO  20170175313 A1  10/2017

OTHER PUBLICATIONS

PCT International Search Report for International Application No. PCT/NL2019/050708, completed Jan. 30, 2020; dated Jun. 2, 2020, 3pp.

(Continued)

*Primary Examiner* — Alvaro E Fortich
(74) *Attorney, Agent, or Firm* — The Roy Gross Law Firm, LLC; Roy Gross

(57) ABSTRACT

During both invasive and non-invasive treatments and therapies, inaccuracies in locating the areas of interest mean that not all the area is treated, or the treatment is incomplete. A magnetic field probe 100, 1010, 102, 103 is provided that improves determination of a disposition of an implantable magnetic marker 200, the probe comprising a first 110, 120 and second 110, 120 magnetic sensor, substantially disposed along a transverse axis intersecting the longitudinal axis of the probe 150. The first 110, 120 and second 110, 120 magnetic sensors are close to the distal end 160 of the probe, (Continued)

and are separated by a minor sensor separation. A third 120, 130 magnetic sensor is provided close to the proximal end 165, separated by a major sensor separation from the second magnetic sensor 110, 120 close to the distal end 160, the major sensor separation being larger than the minor sensor separation; and the ratio of the major sensor separation to the minor sensor separation is in the range 1.25 to 40, preferably in the range 1.6 to 7.6.

In this example, the second magnetic sensor is functionally configured and arranged to co-operate with both the first magnetic sensor and the third magnetic sensor. This may be implemented using three or more magnetic sensors.

This provides a probe capable of accurately determining one or more dispositions of the implantable magnetic marker when the distal end of the probe is close to the marker and also when it is further away.

In particular, including the pair of sensors close to the distal end may increase the sensitivity and accuracy of the probe.

17 Claims, 8 Drawing Sheets

Related U.S. Application Data continuation of application No. PCT/NL2019/050708, filed on Oct. 28, 2019.

(56) References Cited

U.S. PATENT DOCUMENTS

| | | |
|---|---|---|
| 2007/0163367 A1 | 7/2007 | Sherman et al. |
| 2007/0276218 A1 | 11/2007 | Yellen |
| 2010/0174177 A1* | 7/2010 | Wu .................. A61B 5/062 |
| | | 604/523 |
| 2012/0016316 A1 | 1/2012 | Zhuang et al. |
| 2014/0051985 A1 | 2/2014 | Fan et al. |
| 2014/0257746 A1 | 9/2014 | Dunbar et al. |
| 2015/0297114 A1* | 10/2015 | Cox .................. A61B 5/063 |
| | | 600/374 |
| 2018/0055417 A1 | 3/2018 | Munaretto |
| 2019/0038178 A1 | 2/2019 | Sasaki et al. |

OTHER PUBLICATIONS

PCT Written Opinion for International Application No. PCT/NL2019/050708, completed Jan. 30, 2020; dated Jun. 2, 2020, 6pp.

* cited by examiner

MAGNETIC FIELD PROBE FOR DETERMINING A DISPOSITION OF AN IMPLANTABLE MAGNETIC MARKER

CROSS-REFERENCE TO RELATED APPLICATIONS

This application is a Continuation of U.S. Ser. No. 17/322,401, filed May 17, 2021, which is a Track One Continuation of PCT Patent Application No. PCT/NL2019/050708 having International filing date of Oct. 28, 2019, which claims the benefit of Netherlands Patent Application No. NL 2022093, filed Nov. 29, 2018, the contents of which are all incorporated herein by reference in their entirety.

FIELD

The present disclosure relates to a magnetic field probe for determining a disposition of an implantable magnetic marker, a detection unit comprising the probe and a method of detecting the disposition of an implantable magnetic marker.

BACKGROUND

During both invasive and non-invasive treatments and therapies, it is important that health professional be able to accurately locate areas of interest. Frequently, professionals rely on sight and manual manipulation to find and remember areas of interest, often marking an outer surface of skin. In practice, imaging equipment such as X-ray and/or ultrasound, may also be used to assist in the location—however, this relies on being able to distinguish the area of interest from the surrounding tissue using the imaging technologies. Inaccuracies in being able to locate the areas of interest may mean that not all the area is treated, or the treatment is incomplete. This is a problem for both therapeutic and cosmetic procedures and treatments, including removal of tumors, removal of polyps, cosmetic surgery, removal and/or correction of tissues, localization of implanted devices—for example, birth-control devices such as Implanon, may need to be localized.

For example, if lesion resection or removal is prescribed following cancer screening, the surgeon needs to know the location and extent of the lesion. The current golden standard in clinical practice requires the placement of metal anchor wires in the target immediately before the surgical procedure, which risks infection and movement of the wires. Newer solutions use radio-active markers, but the use of radio-active materials is tightly controlled and regulated. Electro-magnetic and RFID (Radio-Frequency Identification) markers have been developed, but these are bulky and prone to failure. Any inaccuracy in locating the area of interest may result in an incomplete resection or removal of the lesion, requiring additional treatments.

In addition, improvements in screening procedures means that smaller and early stage lesions are increasingly being identified in patients—although this early detection is more beneficial to the patient, small lesions may be difficult for the surgeon to identify and locate. They are also likely to be impalpable. Intra-operative imaging is often cumbersome and expensive.

Recently, the use of implantable magnetic markers has been proposed. These provide a higher degree of safety compared to radio-active markers, but it still requires considerable effort by the healthcare professional to detect the disposition (localize) of the marker. This becomes even more difficult when very small magnetic markers are used to mark very small areas of interest.

For example, U.S. Pat. No. 7,561,051B1 describes an apparatus for locating a magnet and/or determining the orientation of the apparatus relative to the magnet. In one embodiment, the apparatus includes a multi-axis magnetic field sensor movable in a reciprocating manner so as to permit sensor readings at multiple spaced locations. In another embodiment, the apparatus includes a plurality of multi-axis magnetic field sensors arrayed along a straight line. The apparatus may be used in a number of medical and other applications, including tissue resection, tracking movement of a medical device in a body cavity and tracking movement of an internal organ.

It is an object of the invention to provide improved determination of a disposition of an implantable magnetic marker.

GENERAL STATEMENTS

According to a first aspect of the present disclosure, there is provided a magnetic field probe for determining a disposition of an implantable magnetic marker, the probe extending along a probe longitudinal axis, the probe comprising a distal end, configured and arranged to be disposed close to an outer surface of skin; a first magnetic sensor close to the distal end; a second magnetic sensor, close to the distal end, configured and arranged to be separated by a minor sensor separation from the first magnetic sensor, the first and second magnetic sensors being configured and arranged to determine, in use, one or more dispositions of the magnetic marker; a third magnetic sensor close to a proximal end, configured and arranged to be separated by a major sensor separation from the second magnetic sensor, the third and second magnetic sensors being configured and arranged to further determine, in use, the one or more dispositions of the magnetic marker; wherein: the major sensor separation is larger than the minor sensor separation; and the ratio of the major sensor separation to the minor sensor separation is in the range 1.25 to 40, preferably in the range 1.6 to 7.6; and the first and second magnetic sensors are substantially disposed along a transverse axis, the transverse axis intersecting the probe longitudinal axis.

Note that the use of the labels first, second, and third for the sensors is distinct and not necessarily the same as the labels first, second and third for the sensor groups. The first, second and third sensors may be selected from any of those groups in accordance with the functionality performed by the different embodiments.

By providing, close to the distal end of the probe, a pair of magnetic sensors with a minor separation along a transverse axis, and a further pair with a major separation, one close to the distal end and the other close to the proximal end, where the ratio of the major sensor separation to the minor sensor separation is in the range 1.25 to 40, preferably in the range 1.6 to 7.6, a probe is provided capable of accurately determining the location (disposition) of the implantable magnetic marker when the distal end of the probe is close to the marker and further away. In particular, including the pair of sensors close to the distal end may increase the sensitivity and accuracy of the probe.

In this example, the second magnetic sensor is functionally configured and arranged to co-operate with both the first magnetic sensor and the third magnetic sensor. This may be implemented using three or more magnetic sensors, as explained below.

Optionally, the transverse axis may be approximately perpendicular to the longitudinal axis. This may simplify calculations of dispositions in some cases.

According to a further aspect, the probe may further comprise a fourth magnetic sensor, close to the distal end, wherein the fourth magnetic sensor is configured and arranged, instead of the second magnetic sensor, to be separated from the third magnetic sensor by the major sensor separation.

It may be convenient to provide an additional (fourth) magnetic sensor, which performs part of the functions of the second sensor in the first aspect, namely co-operating with the third magnetic sensor. The second magnetic sensor is configured and arranged to be separated by a minor sensor separation from the first magnetic sensor.

According to another aspect of the current disclosure, the magnetic sensors configured and arranged to be separated by the major sensor disposition, may be substantially disposed along a longitudinal axis.

Optionally, these sensors may be disposed along the probe longitudinal axis.

Different pairs of magnetic sensors may be configured and arranged to be separated by the major sensor disposition. By disposing such a pair of sensors substantially along a longitudinal axis of the probe, a long, thin probe is provided which is particularly easy to manipulate. By disposing them along the probe longitudinal axis, calculations of dispositions relative to the probe longitudinal axis may be simplified in some cases.

Optionally, the transverse axis may be approximately perpendicular to a longitudinal axis along which sensors are configured and arranged to be separated by a major sensor separation. Optionally this may be the probe longitudinal axis.

This may simplify calculations of dispositions in some cases.

According to yet another aspect of the current disclosure, the probe may comprise the probe further comprises: one or more compensation sensors for measuring a background magnetic field; wherein: the determination, in use, of one or more dispositions of the magnetic marker further considers the background magnetic field.

Advantageously, an existing sensor or a dedicated sensor may be configured to measure (or detect) a background magnetic field, such as the Earth's magnetic field. The disposition determination may be compensated using background measurements to further increase the accuracy and sensitivity.

According to another aspect of the current disclosure, the minor sensor separation and/or the major sensor separation may be predetermined by considering the inverse cube law determination of a magnetic field strength associated with the implantable magnetic marker.

By considering the inverse cube law when determining the longitudinal separation of one or more sensors, the accuracy of the magnetic field measurement and the model and/or curve-fitting may be further improved.

In addition, a method is provided for determining the disposition of an implantable magnetic marker, the method comprising: providing a probe comprising a distal end, configured and arranged to be disposed close to an outer surface of skin, the probe extending along a probe longitudinal axis and further comprising: a first magnetic sensor close to the distal end and a second magnetic sensor, configured and arranged to be separated by a minor sensor separation from the first magnetic sensor, the first and second magnetic sensors being substantially disposed along a transverse axis, the transverse axis intersecting the longitudinal axis; configuring and arranging the first and second magnetic sensors to determine, in use, one or more dispositions of the magnetic marker; the probe further comprising a third magnetic sensor close to a proximal end, configured and arranged to be separated by a major sensor separation from the third magnetic sensor; configuring and arranging the third and second magnetic sensors to further determine, in use, the one or more dispositions of the magnetic marker; wherein: the ratio of the major sensor separation to the minor sensor separation is in the range 1.25 to 40, preferably in the range 1.6 to 7.6.

In this example, the second magnetic sensor is functionally configured and arranged to co-operate with both the first magnetic sensor and the third magnetic sensor. This may be implemented using three or more magnetic sensors, as explained below.

According to a still further aspect, the probe may further comprise a fourth magnetic sensor, close to the distal end, the method comprising: configuring and arranging the fourth magnetic sensor, instead of the second magnetic sensor, to be separated from the third magnetic sensor by the major sensor separation.

It may be convenient to provide an additional (fourth) magnetic sensor, which performs part of the functions of the second sensor in the first aspect, namely co-operating with the third magnetic sensor. The second magnetic sensor is configured and arranged to be separated by a minor sensor separation from the first magnetic sensor.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments and which are not necessarily drawn to scale, wherein.

DETAILED DESCRIPTION

In the following detailed description, numerous non-limiting specific details are given to assist in understanding this disclosure. It will be obvious to a person skilled in the art that the computer processing part of the method may be implemented on any type of standalone system or client-server compatible system containing any type of client, network, server, and database elements.

Figure 1A:
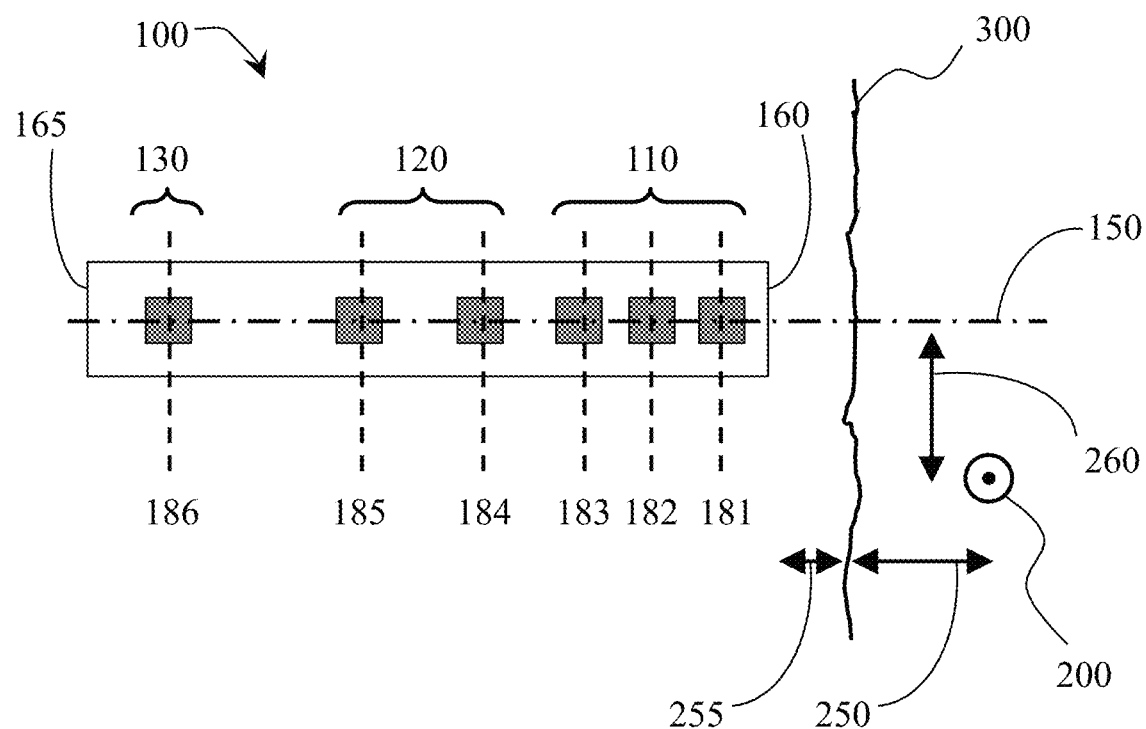
FIGS. 1A and 1B depict an embodiment of a magnetic field probe for detecting the disposition (localizing) of an implantable magnetic marker.
Figure 1B:
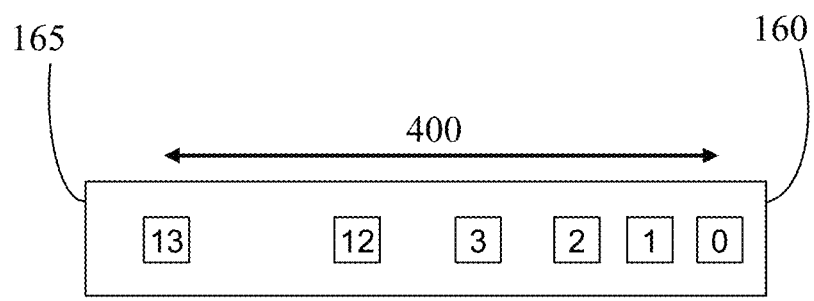

FIG. 1A and FIG. 1B depict a magnetic field probe 100 for detecting a disposition (localizing) of an implantable magnetic marker 200. As depicted, the magnetic marker 200 is implanted below an outer surface of skin 300 to mark an area of interest—this may be a few millimeters or a few centimeters below 250 the outer surface of the skin. This may also be called depth 250. The magnetic field probe may extend along a probe longitudinal axis 150—when extended, it provides a convenient reference point for determining a disposition of the magnetic marker 200. This disposition of the marker 200 may be expressed in any convenient parameter—however, a user may be particularly interested in being provided with a transverse distance 260 between the probe longitudinal axis 150 and the magnetic marker 200, and the longitudinal distance 255, 250 between the distal end 160 and the magnetic marker 200.

The marker may be implanted in any convenient way, such as by injection. The injection may be, for example, into soft tissue or organs, or delivery via a bronchoscope to lung bronchii, or coloscope to colon, or integrated in a swallowable device such as an electronic pill. The method of implantation may depend on, for example, the depth 250 required, the subsequent procedure to be performed, the size of the area of interest, the location of the area of interest, the type of tissue in the area, and the type of tissue surrounding the area. It may be implanted immediately before detection, or some time earlier.

Typically, a suitable magnetic marker 200 is approximately cylindrical:
a diameter of 1.45 mm, a length of 2.19 mm and a remnant field (Br) of 1.43 T (Neodymium N52), or
a diameter of 1.75 mm, a length of 5 mm and a remnant field (Br) of 1.43 T (Neodymium N52).

The probe 100 comprises a distal end 160, configured and arranged to be disposed close to an outer surface of skin 300. The probe 100 is further configured and arranged to determine one or more dispositions (distance) between a probe reference and the magnetic marker 200, as described below. The probe reference may be one or more points of the probe 100, one or more axes of the probe 100, one or more planes of the probe 100, or a combination thereof.

The probe 100 comprises one or more magnetic sensors, configured to measure one or more properties of a magnetic field (for example strength, direction, Bx, By, Bz) generated by the magnetic marker 200. These properties are used to determine the one or more dispositions using a software algorithm.

For example, it may be advantageous for the user if the distal end 160 of the probe 100 was a reference point—in other words, if the probe 100 is configured to determine the one or more dispositions with respect to the distal end 160 of the probe 100. If the probe extends substantially longitudinally, then a long thin probe 100 is provided which is particularly easy to manipulate, and finding the magnetic marker 200 by moving the distal end 160 is more intuitive.

As depicted, the distal end 160 may be disposed at a distance 255 from the outer surface of skin 300—a spacer may be used to maintain a fixed distance 255, or the distance 255 may be zero if the probe 100 is further configured and arranged to contact the outer surface of skin 300. The probe 100 may be further configured and arranged to be pushed against the outer surface of skin 300 to create an indent which may further reduce the distance between the distal end 160 of the probe 100 and the magnetic marker 200. In general, the smaller the distance between the probe 100 and the magnetic marker, the greater the amplitude of any signal measured. For some treatments, the probe 100 may further configured and arranged to be inserted through the outer surface of skin 300 and/or into a body cavity to further reduce the distance between probe 100 and marker 200. This may be, for example, via a surgical incision or via a natural orifice.

The probe 100 may be comprised in a detection unit or device (not shown). It will be clear to the skilled person that functionalities for determining the one or more dispositions may be implemented in the hardware and software of the magnetic probe 100, or they be implemented in the hardware and software of the rest of the detector. The functionalities may also be divided in any convenient way between the magnetic probe 100 and the rest of the detector unit.

A detection unit or device for a probe 100 may comprise one or more of the following:
an optional electrical and/or mechanical connection, configured to attach to a proximal end 165 of the probe 100. It may be advantageous to make the attachment releasable. The connection may also be wireless, configured and arranged to allow at least data transmission between the probe 100 and the rest of the detector;
a power supply to provide energy to the probe magnetic sensors;
a processor, configured to collect magnetic sensor measurement values, and to determine the dispositions using an appropriate software algorithm;
optionally, a display may also be provided to indicate to the user the results of the determination. Preferably, a transverse and/or longitudinal distance to the magnetic marker 200 is displayed, numerically and/or graphically. Additionally or alternatively, a graphical representation may be provided indicating a transverse and/or longitudinal direction. Additionally or alternatively, audio feedback may also be provided—this is described in more detail below. The distances (dispositions) may be displayed, for example, as relative values and/or absolute values. Audio feedback may be provided, for example, similar to the way distance to an object is indicated with an automobile parking sensor with different tones.

The probe 100 comprises three or more magnetic sensors. These may be configured and arranged to be comprised in up to three different groups of sensors 110, 120, 130. As described below, each sensor may be configured and arranged to perform a single function or to contribute to a plurality of functions. In this example, three groups 110, 120, 130 are identifiable based on their position relative to the distal end 160 of the probe 100. FIG. 1B depicts the reference number assigned to each magnetic sensor for ease of reference—in this embodiment, a minimum of three magnetic sensors are provided, and typically six sensors are used in a 1D array. The sensors are grouped as follows:
110: a first group of at least two magnetic sensors, close to the distal end 160 of the probe 100. As depicted in FIG. 1B, these may be sensors 0, 1 and 2. Not all sensors positions need to be occupied—one or more sensor may be physically omitted or disabled in software. These sensors are configured and arranged such that adjacent sensors are longitudinally and transversely separated from each other by a minor sensor separation, such that at least two dispositions of the marker 200 may be determined when the distal end 160 is relatively close to the magnetic marker 200. Sensors 0 and 1 are separated by a minor sensor separation, and sensors 1 and 2 are also separated by a minor sensor separation. Sensors separated by a minor sensor separation are configured and arranged to provide measurements for accurately determining one or more dispositions of the marker 200 when the distal end 160 is relatively close to the magnetic marker 200. In practice, a sensor may approach the magnetic marker 200 to within approximately 2.5 mm at the closest—typically, a housing will be used to enclose the magnetic probe 100 limiting the closest distance that the marker may be approached. For example, when IC magnetic sensors are used such as LGA-12 packages with dimensions of 2×2×0.7 mm, they may be disposed with a gap of 0.5 mm, which provide a minor sensor separation (approximated to the distance between the center of the packages or approximately 2.5 mm). The sensors separated by the minor separation may be optimized for accurate marker 200 disposition determination of between 0.5 and 3 times the length of the marker.

Note that non-adjacent sensors in this embodiment are separated longitudinally by a major sensor separation: sensors 2 and 0.

120: a second group of at least one magnetic sensor. As depicted in FIG. 1B, this may be sensor 3 and 12. These are closer to a proximal end 165 of the probe 100 than the first group 110 (in other words, further away from the distal end 160). They are mainly configured and arranged to provide measurements for determining one or more dispositions (distance) when the distal end 160 of the probe 100 is further away from the magnetic marker 200. The disposition determined using measurements from one or more sensors in the second group is compared to a disposition determined using measurements from one or more sensor from the first group 110—the magnetic sensor from the second group 120 is separated from the magnetic sensor in the first group 110 by a major sensor separation. This major sensor separation is greater than the minor sensor separation. For example, the following are separated by a major sensor separation in a longitudinal direction:
sensors 3 and 0, 1 or 2;
sensors 12 and 0, 1, or 2
sensors 12 and 3

130: optionally, a third group of at least one magnetic sensor. As depicted in FIG. 1B, this may be sensor 13. These are closer to the proximal end 165 of the probe 100 than the second group 120 (in other words, further away from the distal end 160). They may be configured and arranged:
as a compensation sensor. In this case, compensation sensors are mainly configured and arranged to detect a background magnetic field, such as a naturally-occurring magnetic field (from the Earth), a man-made field present due to equipment being operated in the environment where the measurements and determinations are performed, and/or a diamagnetic field created by the tissue in or around the area of interest.
alternatively or additionally, magnetic sensors in the third group 130 may be configured and arranged to provide additional measurements for determining one or more dispositions (distance) when the distal end 160 of the probe 100 is further away from the magnetic marker 200. magnetic sensors from the third group 130 are separated from the first group 110 by a major sensor separation. This major sensor separation is greater than the minor sensor separation, and may be similar, different or equal to any of the other major sensor separations. For example, the following are separated by a major sensor separation in a longitudinal direction: sensors 13 and 0, 1, or 2 magnetic sensors from the third group 130 are separated from the second group 120 by a major sensor separation. This major sensor separation is greater than the minor sensor separation, and may be similar, different or equal to any of the other major sensor separations. For example, the following are separated by a major sensor separation in a longitudinal direction: sensors 13 and 12 or 3.

The terms minor sensor separation and major separation should be interpreted as general categories of separation—a probe 100 may be provided having one or more minor sensor separations and one or more major sensor separations.

A minor sensor separation is in the order of magnitude of the longitudinal length of the magnetic marker 200 to be localized, preferably 0.5 to 3 times this marker length. So, for example, when localizing a marker 2.19 mm long, the minor sensor separation is preferably 1.095 mm to 6.57 mm. When localizing a marker 5 mm long, the minor sensor separation is preferably 2.5 mm to 15 mm.

A major sensor separation is in the order of several times the magnitude of the longitudinal length of the magnetic marker 200 to be localized, preferably 5 to 20 times this marker length. So, for example, when localizing a marker 2.19 mm long, the minor sensor separation is preferably 10.95 mm to 43.8 mm. When localizing a marker 5 mm long, the minor sensor separation is preferably 25 mm to 100 mm.

If a plurality of minor sensor separations is provided, they may be similar, different or equal to each other. If a plurality of major sensor separations is provided, they may be similar, different or equal to each other. However, the major sensor separation is larger than the minor sensor separation and the ratio of the major sensor separation to the minor sensor separation is in the range 1.25 to 40, preferably in the range 1.6 to 7.6.

An advantageous aspect is providing at least two magnetic sensors, separated by a minor sensor separation along a transverse axis—this may provide a high degree of accuracy and/or sensitivity.

Such an "L-configuration" is not known in the art. For example, U.S. Pat. No. 7,561,051 FIG. 2D depicts a 2D configuration, but the approximately transversely-separated sensors are close to the proximal end, and away from the distal end. This is done to keep the probe of U.S. Pat. No. 7,561,051 narrow near the front (distal end), as explained in col 6, lines 11 to 16 of that publication.

The magnetic sensors 0, 1, 2, 3, 12, 13 may be single measurement device, such as a 1D fluxgate measuring a single direction of magnetic field flux. One or more fluxgates may have substantially the same orientation or all may have different orientations—as these orientations and sensitivities are predetermined during the design, the measurement signals from each sensor 0, 1, 2, 3, 12, 13 may be combined with the relative position of the sensors as pre-determined by the design, and one or more selected sensor separations, to determine a disposition of the magnetic marker 200. Alternatively or additionally, the orientations, separations and/or sensitivities may be measured to calibrate an assembled (or partially assembled) probe. The pre-determined and/or calibrated values may be used in a software model and/or a lookup table to determine, in use, one or more dispositions of the magnetic marker 200 relative to a reference point, axis and/or plane of the probe 100.

The separation of sensors 0, 1, 2, 3, 12, 13 may be determined by physical measurement of the distances between the center of the sensor package—for many applications this may be sufficiently accurate, especially if a further calibration of the probe 200 is performed. As depicted in FIG. 1A, the center of the package for sensor 0 lies on a first transverse axis 181, for sensor 1 on a second transverse axis 182, for sensor 2 lies on a third transverse axis 183, for sensor 3 lies on a fourth transverse axis 184, for sensor 12 on a fifth transverse axis 185, and for sensor 13 lies on a sixth transverse axis 186. The transverse axes 181 to 186 are substantially perpendicular to the longitudinal probe axis 150.

The sensor separation is preferably determined in three degrees of freedom, although in some applications one degree of freedom or two degrees of freedom may be sufficiently accurate.

As depicted in FIG. 1A, the magnetic sensors 0, 1, 2, 3, 12, 13 may optionally be disposed along the longitudinal axis 150 of the probe 100. It is particularly advantageous as the longitudinal axis 150 may be used as a reference for the disposition measurements—combining the measurements from the sensors 0, 1, 2, 3, 12, 13 during the determination may then be simplified as the separation is substantially determined by the separation along the longitudinal axis 150.

The magnetic sensors 0, 1, 2, 3, 12, 13 may be configured to measure relative or absolute magnetic intensity, to measure a vector and/or scalar component of a magnetic field. The sensors 0, 1, 2, 3, 12, 13 may be of different types, or one or more sensors 0, 1, 2, 3, 12, 13 may be the same. Each sensor 0, 1, 2, 3, 12, 13 comprises at least one (1D) magnetic detector. The positions may be predetermined by the design and/or measured after the probe is assembled. Additionally or alternatively, technical specifications provided by the sensor manufacturer may be used and/or simulation. Preferably, each sensor measures a vector or 3D magnetic field—this provides the most data to determine (or to reconstruct) the marker's disposition.

Preferably each magnetic sensor 0, 1, 2, 3, 12, 13 is a device comprising two (2D), three (3D or 3-axis) or more magnetic detectors, such as an IC comprising three (3D) substantially mutually perpendicular detectors, providing measurement of three degrees of freedom at approximately the same physical position in the probe. Again, these positions may be predetermined by the design and/or measured after the probe is (partially) assembled. Additionally or alternatively, technical specifications provided by the sensor manufacturer may be used and/or simulation.

In this disclosure, a sensor and detector are often used interchangeably. A sensor is typically a single encapsulated package comprising one or more detectors. If a sensor package comprises two detectors with a physical separation between the detectors sufficiently large to be considered a minor sensor separation, then in the terms of this disclosure, such a sensor package comprises two sensors—each of the detectors provides a measurement of a magnetic field property of the marker 200 relating to a different position within the probe 100. A minor sensor separation is in the order of magnitude of the longitudinal length of the magnetic marker 200 to be localized, preferably 0.5 to 3 times this marker length. If the physical separation between the detectors is too small to be considered a minor sensor separation, then in the terms of this disclosure, such a sensor package comprises one sensor—each of the detectors provides a measurement of a magnetic field property of the magnetic marker 200 relating to the same position within the probe 100.

These detectors may be any suitable type, such as magnetometers, flux gate sensors, geomagnetic sensors, Lorentz force digital MEMS, magneto-inductive sensors, magneto-resistive sensors, Hall sensors, magnetic tunnel junctions and any combination thereof. Many IC packages are available which are small and contain 3 axis detection. So a 'many-axis' solution may be provided with simple PCB design and preferably a smaller probe diameter. The sensor packages proposed below are examples. They are digital and therefore relatively straightforward to interface as less analog design is required.

TI DRV425 Flux Gate Sensor (1D)
Technology: Flux gate
Size: 4×4×0.8 mm
Range: +/−2 mT (single axis)
Resolution: (analogue, depends on ADC)
RMS noise: 0.42 uT @ 1000 Hz (0.2 uT @ 50 Hz)
Offset: 8.3 uT, +1.4 uT hysteresis+0.4 temperature drift
Gain error: 0.3%
Abs Max Field: >2 T in any direction
Note: The offset may be reduced by using a correction sensor with a good zero-field offset performance. Another type of sensor, for example, may be integrated in the probe 100 provide a degree of offset and/or drift correction for the fluxgates. Preferably, such a correction sensor is located close to, or at, the proximal end to reduce the influence of a magnetic field property of the magnetic marker 200.

Bosch BMM1150 3-Axis Digital Geomagnetic Sensor (3D)
Technology: FlipCore
Size: 1.56×1.56×0.6 mm
Range: +/−1.2 mT (x,y); +/−2 mT (z)
Resolution: 0.3 uT (LSB)
RMS noise: 0.3 uT @ 20 samples/s
Offset: 40 uT without Software compensation, 2 uT after compensation (typical)
Gain error: 5% (after compensation)
Abs Max Field: >7 T in any direction ST LIS3MDL (1D)
Technology: Lorentz force digital MEMS
Size: 2×2×1 mm
Range: +/−1.6 mT (x,y,z) (user selectable 0.4, 0.8, 1.2 mT)
Resolution: 0.015 uT (LSB) (@0.4 mT range; 0.06 uT @ 1.6 mT range)
RMS noise: 0.3 uT(x,y); 0.4 uT(z) @ 1.2 mT range
Offset: 100 uT; drifts when fields >5 mT applied
Gain error: 0.15% Full Scale (best fit straight-line non-linearity)
Abs Max Field: <0.1 T in any direction ST IIS2MDC (3D)
Technology: 3-axis digital output magnetometer high-accuracy, ultra-low power
Noise: 0.3 uT with low-pass filter or offset cancellation enabled. 1 SD at 20 samples per second.
Offset error: 6 uT; correctable to 1.2 uT over 20 degree C. range. Hysteresis measured at 3 T was 53 uT and 13 uT with a 5 mT field.
Offset change: with temperature 0.03 uT per degrees C.
Gain error: 1.5% (typical), 7% (max)
Gain change: with temperature 0.03% per degrees C.

Melexis MLX90393 Micropower Triaxis Magnetometer (3D)
Technology: Hall
Size: 3×3×1 mm
Range: +/−5-50 mT (x,y,z) (user selectable)
Resolution: 0.16 uT(x,y); 0.3 uT(z) (LSB)
RMS noise: 0.7 uT(x,y); 0.9 uT(z) @ 50 Sample/s
Offset: 0 uT (?) 2.7 uT/C temperature drift (on-chip compensation available)

Gain error: <1% cross axis sensitivity+3% over temperature
Abs Max Field: -
MEMSIC MMC3416xPJ (3D)
Technology: AMR
Size: 1.6×1.6×0.6 mm
Range: +/−1.6 mT (x,y,z) (user selectable 0.4, 0.8, 1.2 mT)
Resolution: 0.015 uT (LSB) (@0.4 mT range; 0.06 uT @ 1.6 mT range)
RMS noise: 0.15 uT @ 125 samples/s
Offset: Repeatability Error 0.1% Full scale=1.6 uT
Gain error:
Abs Max Field: IT
AKM AK09970N (3D)
Technology: HALL
Size: 3×3×0.6 mm
Range: +/−36 mT (x,y); +/−102 mT (z)
Resolution: 1.1 uT (LSB)
RMS noise: 5 uT @ 100 samples/s
Offset: 743 uT (x,y), 1050 uT (z)
Gain error: 10%
Abs Max Field:
PNI RM3100 Sensor System (3D)
Technology: Magneto-inductive
Size: 15.24×12.8×3×10.5 mm
Range: +/−800 uT(z)
Resolution: 13 nT (LSB)
RMS noise: 15 nT @ 100 samples/s
Offset: Repeatability 8 nT hysteresis 15 nT
Gain error: linearity 0.5%
Abs Max Field: -
Note: Sensor system contains 3 coils and a driver IC with digital interface
Longitudinal sensor array lengths 400 of 40 mm to 50 mm are preferred.

Each sensor 0, 1, 2, 3, 12, 13 comprises one or more detectors and measures respectively one or more magnetic properties of the magnetic marker 200. These property measurements are provided to a software algorithm which combines them, together with physical parameters such as orientation, sensitivity, sensor separation distance, to determine the one or more dispositions of the magnetic marker 200 relative to the sensor position within the probe 100.

In some applications, triangulation principles may provide sufficient accuracy to determine one or more dispositions of the marker 200. Each sensor 0, 1, 2, 3, 12, 13 measurement may be converted to a disposition to the magnetic marker 200, by considering the marker to be at a point on a sphere of radius r from each sensor. With two sensors 0, 1, 2, 3, 12, 13, the magnetic marker 200 may be anywhere along a circle where the two spheres intersect. In practice, the presence of noise may cause the circular intersection to be a ring-like volume. With three sensors, the three spheres may intersect at a point (or approximately at a point)—in some applications, this may be sufficiently accurate enough for marker localization.

Preferably, a 3D model of the marker magnetic field is pre-determined by simulation and/or measurement. The sensor measurements of magnetic properties combined with the physical properties/locations, are then fitted to the 3D model, using, for example, one or more curve fitting algorithms, to determine the one or more dispositions. This 3D-model approach is advantageous as higher degrees of disposition determination may be provided.

Figure 5:
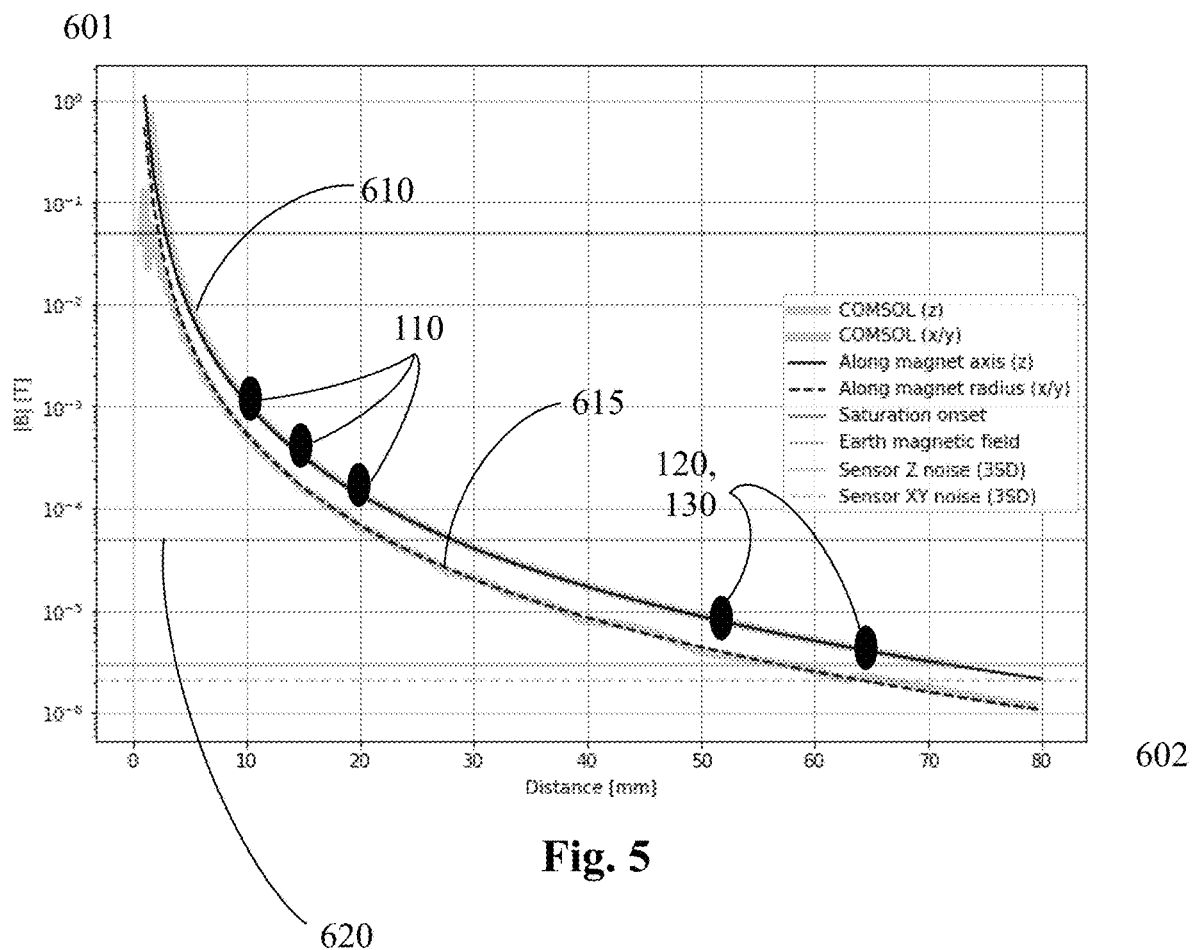
FIG. 5 shows the expected variation in the magnetic field of a first marker and some possible sensor separations.

To explain the basic principle, FIG. 5 depicts a finite element model of the magnetic field of a magnetic marker 200 and how measurements may be used to determine one or more dispositions. As depicted, the magnetic field measured 601 in T varies with distance in mm 602 from the magnetic marker 200. In this case, the finite element model is calculated for a cylindrical magnet marker 200 with diameter 1.45 mm, length 2.19 mm and remanence Br of 1.43 T.

Two curve examples are depicted: the distance along the longitudinal axis (length) 610 of the magnetic marker 200, and the distance along the radial axis (radius) 620 of the magnetic marker 200. As the orientation of the magnetic marker 200 is usually not predetermined, the probe 100 is preferably configured to fit the sensor measurement data to both models—for example, in this illustration, the probe 100 is configured to fit both curves to determine a disposition to the marker 200.

As depicted, the magnetic field strength 610, 615 drops rapidly as $1/r^3$ (the inverse cube law).

One of the insights on which the invention is based is that it is advantageous to vary the separation of the magnetic sensors—at the steep part of the curve 610, 615 where the distal end 160 is close to the magnetic marker 200, sensors may be provided with one or more minor sensor separations—these are indicated as being comprised in the first group 110 and benefit from the expected better Signal-to-Noise Ratio (SNR). At the flatter part of the curve 610, 615 where the distal end 160 is further away from the magnetic marker 200, sensors may be provided with one or more major sensor separation—these are indicated as being comprised in the second group 120, 130—the greater sensor separation may provide a better Signal-to-Noise Ratio (SNR) than when the same sensor separation is used at all positions.

By using the sensor measurements, with additional parameters such as sensor separation, sensitivity and orientation, the measurements may be fitted to one or more curves 610, 615, thereby fitting the measurement data to the 3D-model. Once an acceptable correlation is achieved, the distance (disposition) between the probe 200 and the magnetic marker 200 may be estimated—preferably both a longitudinal and a transverse disposition are determined.

The 3D-models, and any curve 610, 615, may be established from manufacturers' technical data, from simulation, from measurement or any combination thereof.

As depicted, the magnetic field strength 610, 615 for this particular magnetic marker 200, becomes weaker than the Earth's magnetic field 620 at a distance of 30 mm from the marker 200. To improve detection accuracy at comparable distances, the sensor measurements may be advantageously compensated for any background magnetic field, such as the Earth's magnetic field 620.

The ratio of the major sensor separation to the minor sensor separation is in the range 1.25 to 40, preferably in the range 1.6 to 7.6. This provides a high degree of measurement accuracy when the distal end 160 of the probe 200 is close (20 mm or less) from the magnetic marker 200 and when the distal end 160 is further away (30 mm or more).

It may further be advantageous to predetermine the minor and/or major sensor separation by considering the inverse cube law for the magnetic marker 200 being localized. This may improve the accuracy and speed of the curve 610, 615 fitting process.

Figure 6:
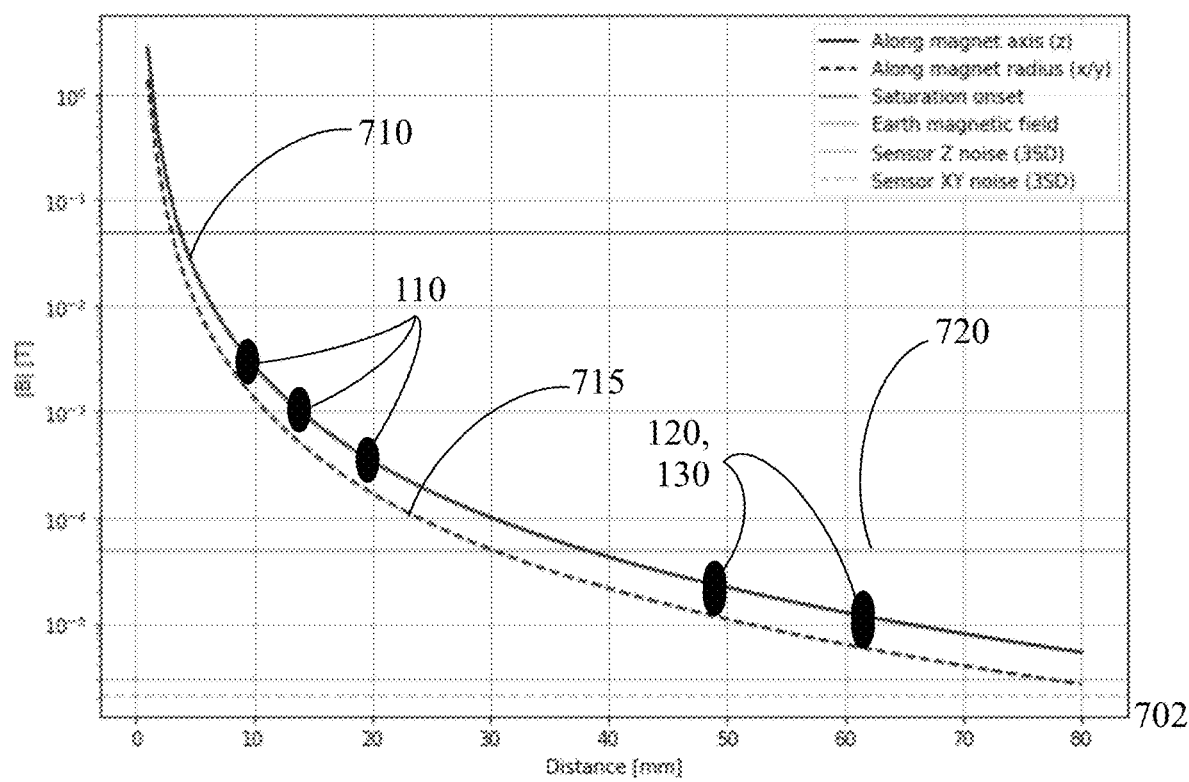
FIG. 6 shows the expected variation in the magnetic field of a second marker and some possible sensor separations.

In a second example, a 3D model of a magnetic field of a different magnetic marker is pre-determined by simulation and/or measurement. The sensor measurements of magnetic properties combined with the physical properties/locations, are then fitted to the 3D model, using, for example, one or more curve fitting algorithm depicted in FIG. 6. A finite element model of the magnetic field of a different magnetic marker 200 is depicted. The magnetic field measured 701 in T varies with distance in mm 702 from the magnetic marker 200. In this case, the finite element model is calculated for a cylindrical magnet marker 200 with diameter 1.75 mm, length 5 mm and remanence Br of 1.43 T.

Two curve examples are again depicted: the distance along the longitudinal axis (length) 710 of the magnetic marker 200, and the distance along the radial axis (radius) 720 of the magnetic marker 200. As the orientation of the magnetic marker 200 is usually not predetermined, the probe 100 is preferably configured to fit the sensor measurement data of both models—for example, in this illustration, the probe 100 is configured to fit both curves to determine a disposition to the marker 200.

As depicted, the magnetic field strength 710, 715 also drops rapidly as $1/r^3$ (the inverse cube law)

Similar to FIG. 5, the separation of the magnetic sensors is varied—at the steep part of the curve 710, 715 where the distal end 160 is close to the magnetic marker 200, sensors may be provided with one or more minor sensor separations—these are indicated as being comprised in the first group 110. At the flatter part of the curve 710, 715 where the distal end 160 is further away from the magnetic marker 200, sensors may be provided with one or more major sensor separation—these are indicated as being comprised in the second group 120, 130.

The 3D models and any curves 710, 715 may be established from manufacturers' technical data, from simulation, from measurement or any combination thereof.

As depicted, the magnetic field strength 710, 715 for this particular magnetic marker 200, becomes weaker than the Earth's magnetic field 720 at a distance of 40 mm from the marker 200. To improve detection accuracy at comparable distances, the sensor measurements may be advantageously compensated for any background magnetic field, such as the Earth's magnetic field 720.

The ratio of the major sensor separation to the minor sensor separation is again in the range 1.25 to 40, preferably in the range 1.6 to 7.6. This again provides a high degree of measurement accuracy when the distal end 160 of the probe 200 is close (20 mm or less) from the magnetic marker 200 and when the distal end 160 is further away (30 mm or more).

As mentioned for FIG. 5, it may further be advantageous to predetermine the minor and/or major sensor separation by considering the inverse cube law for the magnetic marker 200 being localized.

Figure 2A:
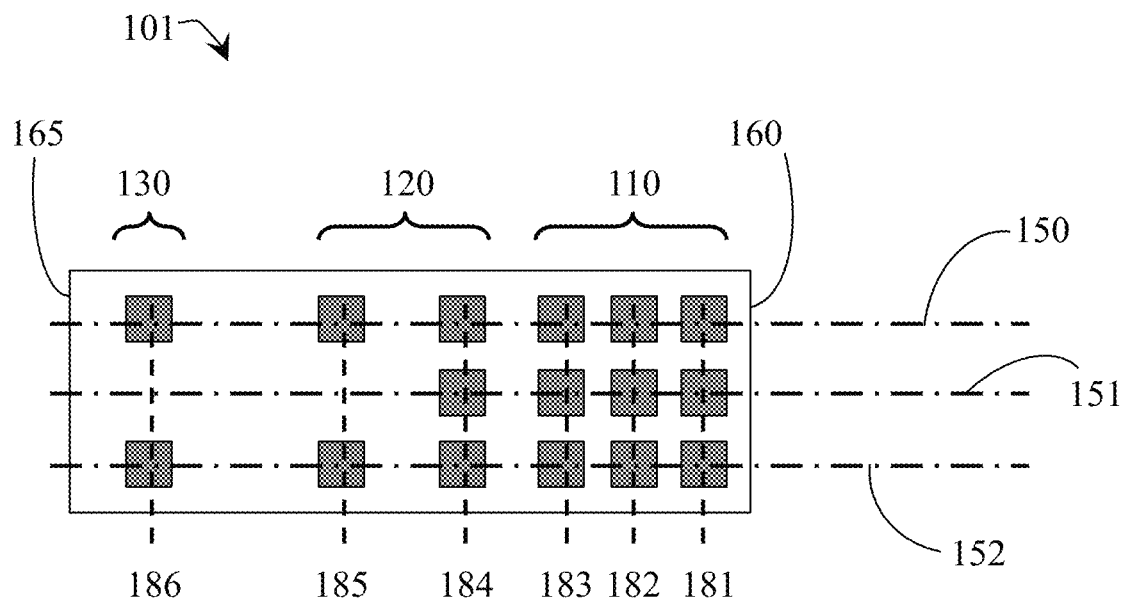
FIGS. 2A and 2B depict a second embodiment of magnetic field probe.

FIG. 2A depicts a further embodiment 101 of the probe—for clarity, the magnetic marker 200 being localized and the skin 300 are not depicted. However, the measurement situation is analogous to the situation depicted in FIG. 1A.

Figure 2B:
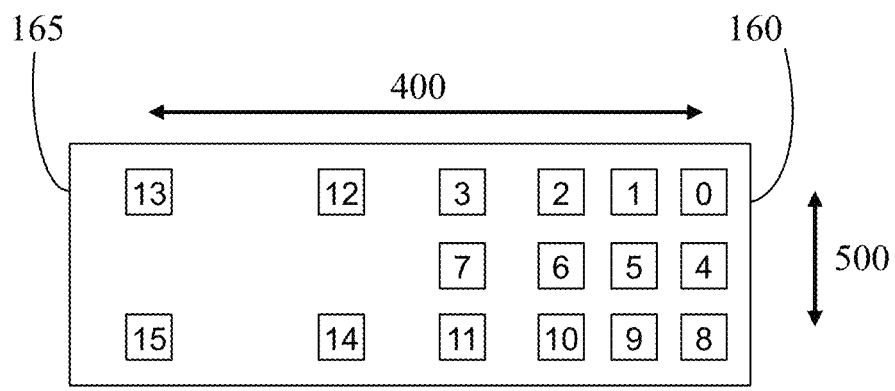

The probe 101 comprises a distal end 160, configured and arranged to be disposed close to an outer surface of skin 300. The probe 101 further comprises three rows of two or more magnetic sensors. These may be configured and arranged to be comprised in up to three different groups of sensors 110, 120, 130. As described below, each sensor may be configured and arranged to perform a single function or to contribute to a plurality of functions. The three groups explained above with reference to FIG. 1A are also present, although not all rows comprise sensors in each group. FIG. 2B depicts the reference number assigned to each magnetic sensor for ease of reference—in this embodiment, a minimum of six magnetic sensors are provided, and typically sixteen sensors are used in a 2D array. The sensors are grouped as follows:

110: a first group of at least two magnetic sensors, close to the distal end 160 of the probe 101. As depicted in FIG. 2B, these may be sensors 0, 1, 2, 4, 5, 6, 8, 9 and 10 in a 3×3 2D array. Not all sensors positions need to be occupied in practice—one or more sensors in the 3×3 2D array may be physically omitted or disabled in software. These sensors are configured and arranged such that adjacent sensors are separated from each other by a minor sensor separation in both longitudinal and transverse directions.

However, by combining measurements from non-adjacent sensors, one or more sensors in the first group 110 may be considered to be separated by a major sensor separation in a transverse direction. For example, the following are separated transversely by a major sensor separation:

sensors 2 and 10;
sensors 1 and 9;
sensors 0 and 8;

Similarly, the following are separated longitudinally by a major sensor separation:

sensors 2 and 1;
sensors 6 and 4;
sensors 10 and 8;

120: a second group of at least one magnetic sensor. As depicted in FIG. 2B, this may be sensors 3, 12, 7, 11 and 14 in a 2×3 2D array. Not all sensors positions need to be occupied in practice—one or more sensors in the s×3 2D array may be physically omitted or disabled in software—in FIG. 2B, for example, there is no sensor between 12 and 14. These sensors 120 are closer to a proximal end 165 of the probe 101 than the first group 110 (in other words, further away from the distal end 160). In this embodiment, a magnetic sensor from the second group 120 is longitudinally separated from the first group 110 by a major sensor separation. The major sensor separation is again greater than the minor sensor separation. For example, the following are separated longitudinally by a major sensor separation:

sensors 3 and 0, 1 or 2;
sensors 7 and 4, 5 or 6;
sensors 11 and 8, 9 or 10;
sensors 12 and 0, 1, or 2;
sensors 12 and 3;
sensors 14 and 8, 9, or 10;
sensors 14 and 11;

In addition, one or more sensors in the second group 120 may be separated by a major sensor separation in a transverse direction. For example, the following are separated transversely by a major sensor separation:

sensors 3 and 11;
sensors 12 and 14;

130: optionally, a third group of at least one magnetic sensor is provided. As depicted in FIG. 2B, this may be sensors 13 and 15 in a 1×3 1D array. Not all sensors positions need to be occupied in practice—one or more sensors in the 1×3 2D array may be physically omitted or disabled in software—in FIG. 2B, for example, there is no sensor between 13 and 15. These sensors 130 are closer to the proximal end 165 of the probe 101 than the second group 120 (in other words, further away from the distal end 160). They may be configured and arranged:

as a compensation sensor, as described above in reference to FIG. 1A.

alternatively or additionally, magnetic sensors in the third group 130 may be configured and arranged to provide measurements to determine one or more dispositions (distance) when the distal end 160 of the probe 101 is further away from the magnetic marker 200. For example, the following are separated by a major sensor separation:

sensors 13 and 0, 1, or 2;
sensors 15 and 8, 9, or 10;

For example, the following may be separated by a major sensor separation in a longitudinal direction:

sensors 13 and 12 or 3;
sensors 15 and 14 or 11;

In addition, one or more sensors in the third group 130 may be separated by a major sensor separation in a transverse direction. For example, the following are separated transversely by a major sensor separation: sensors 13 and 15.

As depicted in FIG. 2A, the center of the packages may optionally be disposed along one of more transverse axes. Sensors 0, 4, 8 may lie on a first transverse axis 181, sensors 1, 5, 9 on a second transverse axis 182, sensors 2, 6, 10 on a third transverse axis 183, sensors 3, 7, 11 on a fourth transverse axis 184, for sensor 12, 14 on a fifth transverse axis 185, and sensor 13, 15 lies on a sixth transverse axis 186. The transverse axes 181 to 186 are substantially perpendicular to the longitudinal probe axis 150. Combining the measurements from the sensors may then be simplified as the transverse separation is substantially determined by the separation along the respective longitudinal axes 150, 151, 152.

As depicted in FIG. 2A, the magnetic sensors 0, 1, 2, 3, 12, 13 may optionally be disposed along the longitudinal axis 150 of the probe 101. In addition, magnetic sensors 0, 1, 2, 3, 12, 13 may optionally be disposed along a second longitudinal axis 151 of the probe 101, and magnetic sensors 0, 1, 2, 3, 12, 13 may optionally be disposed along a third longitudinal axis 152 of the probe 101. Combining the measurements from the sensors may then be simplified as the longitudinal separation is substantially determined by the separation along the respective longitudinal axes 150, 151, 152.

It is particularly advantageous if one of the longitudinal axes 150, 151, 152 may be used as a reference for the disposition determination—combining the measurements from the sensors may then be simplified as the separation is substantially determined by the separation along the longitudinal axes 150, 151, 152 used as reference.

Simulations using arrays of the ST IIS2MDC (3D) sensors were performed—each of these sensor package measures three degrees of freedom using three detectors. As the detectors are very close together, effectively measuring at a single position of the probe, each package is considered a magnetic sensor as described in this disclosure.

Figure 7A:
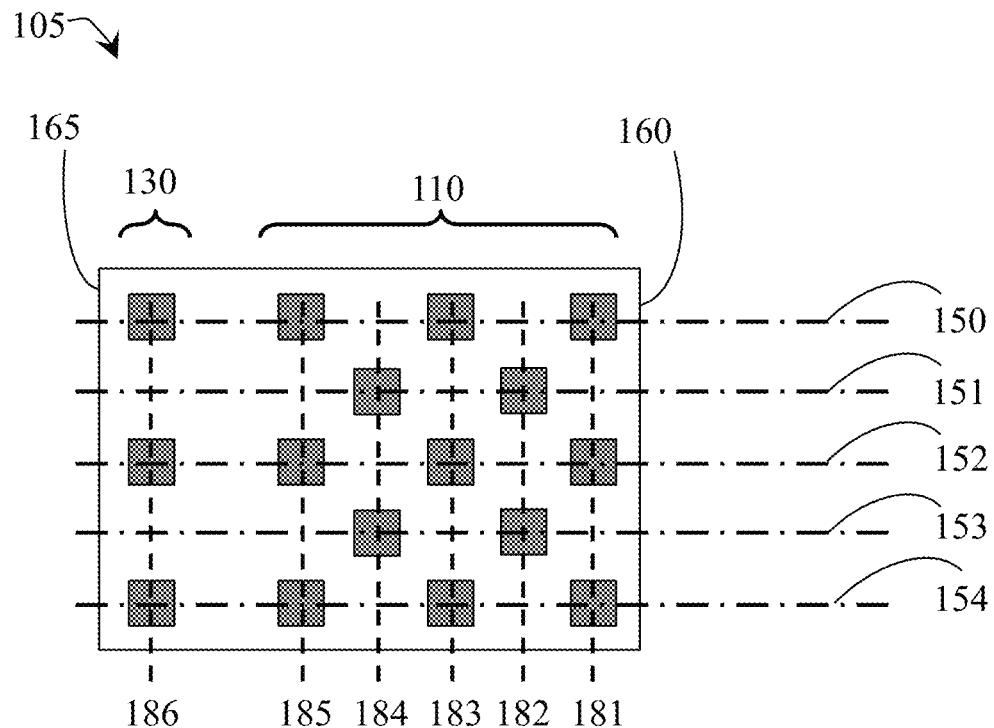
FIGS. 7A and 7B depicts an alternative sensor 2-deminsional arrangement.
Figure 7B:
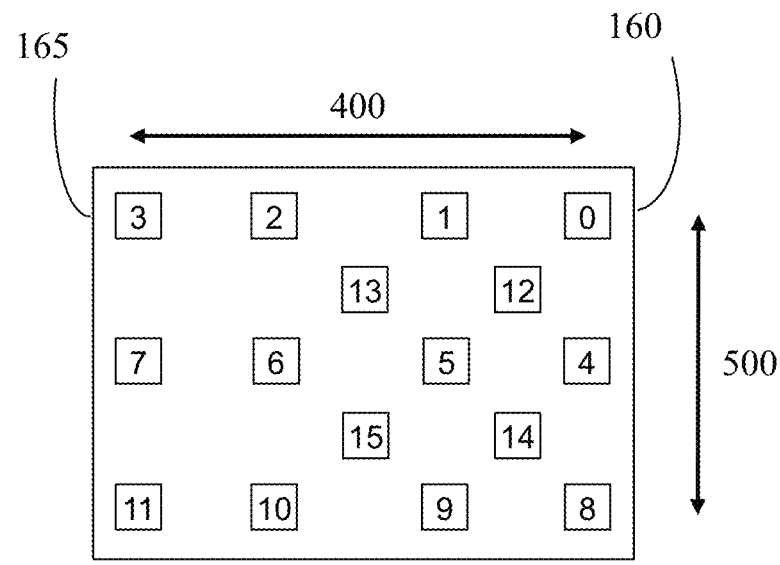

The package size is 2 mm×2 mm×0.7 mm—this means that with at least 0.5 mm space between sensor packages, the minimum sensor separation is approximately 2.5 mm. The following configurations produced satisfactory results:

1. Sensor layout: as depicted in FIGS. 2A and 2B with sensors disposed along three longitudinal axes 150 to 152, and six transverse axes 181 to 186
   Longitudinal array length 400: approx. 40 mm
   Transverse array width 500: approx. 10 mm
   Minor sensor separation in group 110: approx. 5 mm
   Distance between transverse axes 181 and 182: approx. 5 mm
   Distance between transverse axes 182 and 183: approx. 5 mm
   Distance between transverse axes 183 and 184: approx. 6.67 mm
   Distance between transverse axes 184 and 185: approx. 10 mm
   Distance between transverse axes 185 and 186: approx. 15 mm
2. Sensor layout: as depicted in FIGS. 2A and 2B with sensors disposed along three longitudinal axes 150 to 152, and six transverse axes 181 to 186
   Longitudinal array length 400: approx. 50 mm
   Transverse array width 500: approx. 10 mm
   Minor sensor separation in group 110: approx. 5 mm
   Distance between transverse axes 181 and 182: approx. 5 mm
   Distance between transverse axes 182 and 183: approx. 5 mm
   Distance between transverse axes 183 and 184: approx. 10 mm
   Distance between transverse axes 184 and 185: approx. 15 mm
   Distance between transverse axes 185 and 186: approx. 15 mm
3. Sensor layout: as depicted in FIGS. 2A and 2B with sensors disposed along three longitudinal axes 150 to 152, and six transverse axes 181 to 186
   Longitudinal array length 400: approx. 40 mm
   Transverse array width 500: approx. 5 mm
   Longitudinal minor sensor separation in group 110: approx. 5 mm
   Transverse minor sensor separation in group 110: approx. 2.55 mm
   Distance between transverse axes 181 and 182: approx. 5 mm
   Distance between transverse axes 182 and 183: approx. 5 mm
   Distance between transverse axes 183 and 184: approx. 6.67 mm
   Distance between transverse axes 184 and 185: approx. 10 mm
   Distance between transverse axes 185 and 186: approx. 15 mm FIGS. 7A and 7B depict a further embodiment 105 of a probe with an alternative sensor layout—for clarity, the magnetic marker 200 being localized and the skin 300 are not depicted. However, the measurement situation is analogous to the situation depicted in FIG. 1A and FIG. 2A

The probe 105 comprises a distal end 160, configured and arranged to be disposed close to an outer surface of skin 300. The probe 105 further comprises five rows of two or more magnetic sensors. These may be configured and arranged to be comprised in up to two different groups of sensors 110, 130. As described below, each sensor may be configured and arranged to perform a single function or to contribute to a plurality of functions. Two of the three groups explained above with reference to FIG. 1A and FIG. 2A are also present, although not all rows comprise sensors in each group. FIG. 7B depicts the reference number assigned to each magnetic sensor for ease of reference—in this embodiment, a minimum of six magnetic sensors are provided, and typically sixteen sensors are used in a 2D array. The sensors are grouped as follows:

110: a first group of at least two magnetic sensors, close to the distal end 160 of the probe 105. As depicted in FIG. 7B, these may be sensors 0, 1, 2, 4, 5, 6, 8, 9, 10, 12, 13, 14 and 15 in a 5×5 2D array. Not all sensors positions need to be occupied in practice—one or more sensors in the 5×5 2D array may be physically omitted or disabled in software. These sensors are configured and arranged such that adjacent sensors are separated from each other by a minor sensor separation in both longitudinal and transverse directions. Adjacent sensors are diagonally adjacent to each other.

However, by combining measurements from non-adjacent sensors, one or more sensors in the first group 110 may be considered to be separated by a major sensor separation in a transverse direction. For example, the following are separated transversely by a major sensor separation:

sensors 3 and 7, 7 and 11, 2 and 6, 6 and 10, 1 and 5, 5 and 9, 0 and 4, 4 and 8;
separation:
sensors 13 and 15, 12 and 14;

Similarly, the following are separated longitudinally by a major sensor sensors 0 and 1, 1 and 2, 2 and 3, 4 and 5, 5 and 6, 6 and 7, 8 and 9, 9 and 10, 10 and 11;
sensors 14 and 15, 12 and 13

130: optionally, a third group of at least one magnetic sensor is provided, as described above with reference to FIG. 1A and FIG. 2A.

Figure 8A:
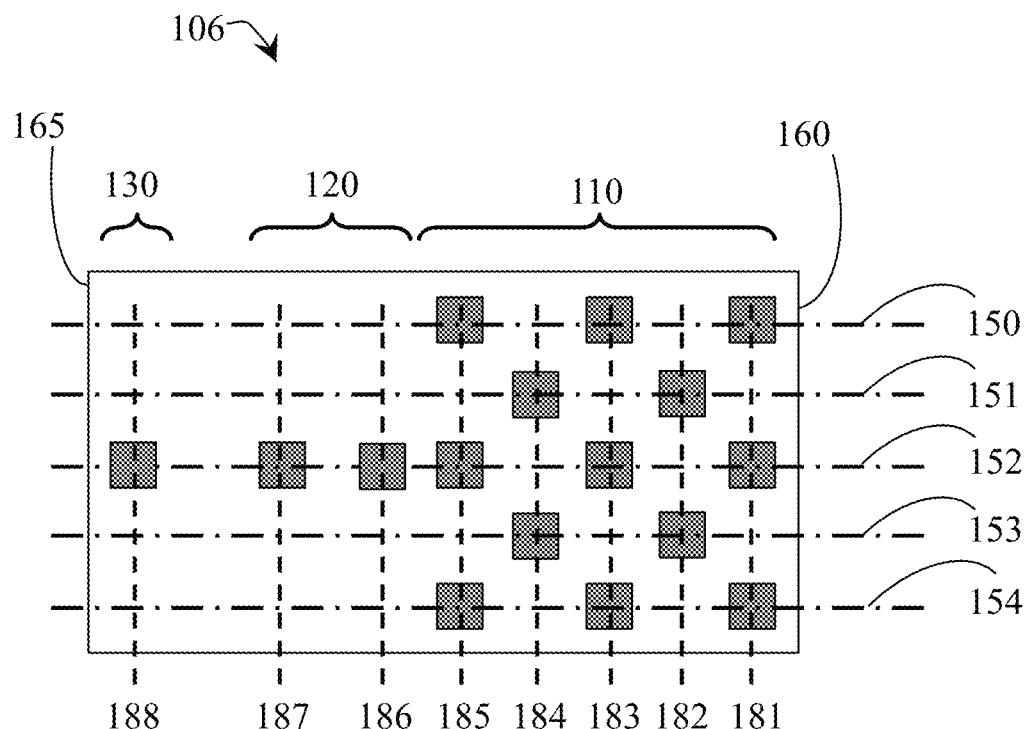
FIGS. 8A and 8B shows a further alternative sensor 2-deminsional arrangement.
Figure 8B:
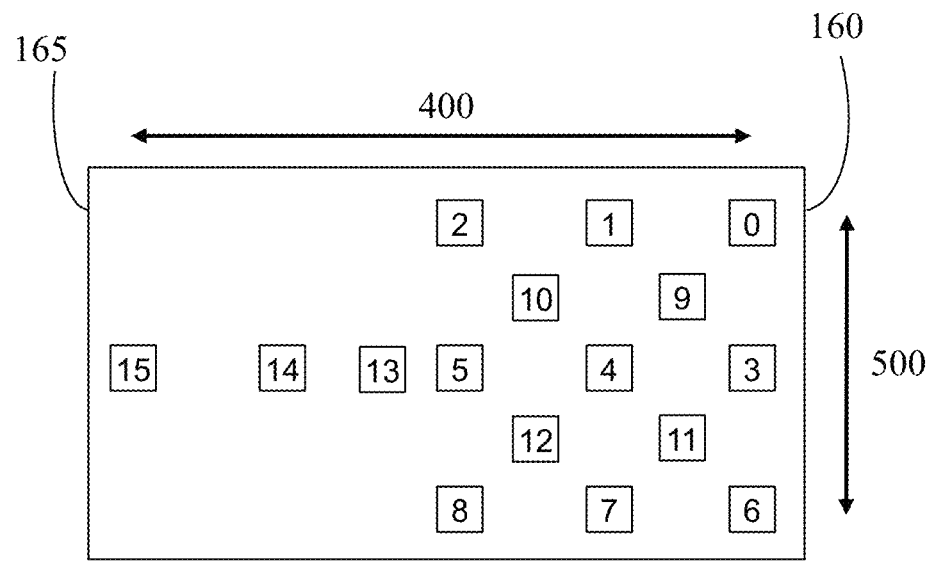

Simulations using arrays of the ST IIS2MDC (3D) sensors were also performed with these alternative layouts:

4. Sensor layout: as depicted in FIGS. 7A and 7B with sensors disposed along five longitudinal axes 150 to 154, and six transverse axes 181 to 186.
   Note: satisfactory results were obtained from this shorter array after subtracting the background field measured using one or more sensors in group 130.
   Longitudinal array length 400: approx. 15 mm
   Transverse array width 500: approx. 10 mm
   Minor sensor separation in group 110: approx. 3.5 mm
   Distance between transverse axes 181 and 182: approx. 3.5 mm
   Distance between transverse axes 182 and 183: approx. 3.5 mm
   Distance between transverse axes 183 and 184: approx. 3.5 mm
   Distance between transverse axes 184 and 185: approx. 3.5 mm
   Distance between transverse axes 185 and 186: approx. 7 mm FIGS. 8A and 8B depict a further embodiment 106 of a probe with an alternative sensor layout—for clarity, the magnetic marker 200 being localized and the skin 300 are not depicted. However, the measurement situation is analogous to the situation depicted in FIG. 1A, FIG. 2A and FIG. 7A

The probe 105 comprises a distal end 160, configured and arranged to be disposed close to an outer surface of skin 300. The probe 106 further comprises five rows of two or more magnetic sensors. These may be configured and arranged to be comprised in up three different groups of sensors 110, 120, 130. As described below, each sensor may be configured and arranged to perform a single function or to contribute to a plurality of functions. The three groups explained above with reference to FIG. 1A and FIG. 2A are also present, although not all rows comprise sensors in each group. FIG. 8B depicts the reference number assigned to each magnetic sensor for ease of reference—in this embodiment, a minimum of six magnetic sensors are provided, and typically sixteen sensors are used in a 2D array. The sensors are grouped as follows:

110: a first group of at least two magnetic sensors, close to the distal end 160 of the probe 106. As depicted in FIG. 8B, these may be sensors 0, 1, 2, 3, 4, 5, 6, 7, 8, 9, 10, 11, 12 in a 5×5 2D array. Not all sensors positions need to be occupied in practice—one or more sensors in the 5×5 2D array may be physically omitted or disabled in software. These sensors are configured and arranged such that adjacent sensors are separated from each other by a minor sensor separation in both longitudinal and transverse directions. Adjacent sensors are diagonally adjacent to each other.

However, by combining measurements from non-adjacent sensors, one or more sensors in the first group 110 may be considered to be separated by a major sensor separation in a transverse direction. For example, the following are separated transversely by a major sensor separation:

sensors 2 and 5, 5 and 8, 1 and 4, 4 and 7, 0 and 3, 3 and 6;
sensors 10 and 12, 9 and 11;

Similarly, the following are separated longitudinally by a major sensor separation:

sensors 0 and 1, 1 and 2, 3 and 4, 4 and 5, 6 and 7, 7 and 8;
sensors 9 and 10, 11 and 12
sensors 13 and 5;
sensors 14 and 15, 14 and 13

130: optionally, a third group of at least one magnetic sensor is provided, as described above with reference to FIG. 1A and FIG. 2A.

Simulations using arrays of the ST IIS2MDC (3D) sensors were also performed with these alternative layouts:

5. Sensor layout: as depicted in FIGS. 8A and 8B with sensors disposed along five longitudinal axes 150 to 154, and eight transverse axes 181 to 188.
   Longitudinal array length 400: approx. 40 mm
   Transverse array width 500: approx. 10 mm
   Minor sensor separation in group 110: approx. 5 mm
   Distance between transverse axes 181 and 182: approx. 5 mm
   Distance between transverse axes 182 and 183: approx. 5 mm
   Distance between transverse axes 183 and 184: approx. 5 mm
   Distance between transverse axes 184 and 185: approx. 5 mm
   Distance between transverse axes 185 and 186: approx. 5 mm
   Distance between transverse axes 186 and 187: approx. 10 mm
   Distance between transverse axes 187 and 188: approx. 15 mm Some conventional detectors and probes require a high remanence (Br) for the magnetic markers 200 due to their low sensitivity—the probe according to the invention allows a higher sensitivity of magnetic marker detection, allowing a broader range of markers to be localized at both close distances and further away.

Figure 3A:
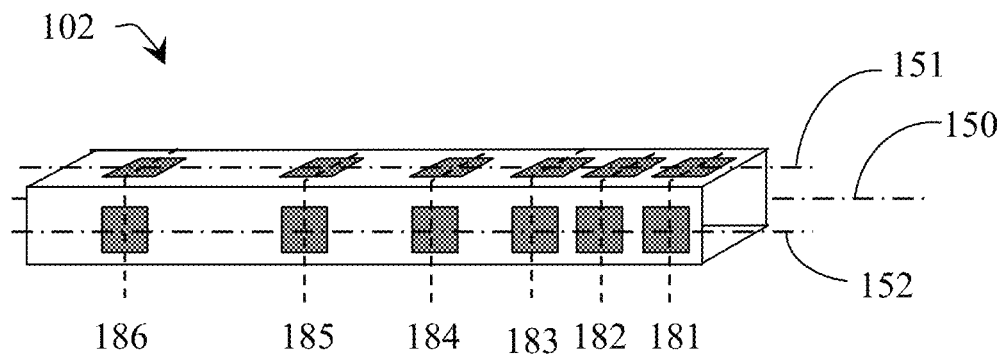
FIGS. 3A, 3B and 3C depicts examples of longitudinally-extended probes with 3-dimensional sensor arrangements.
Figure 3B:
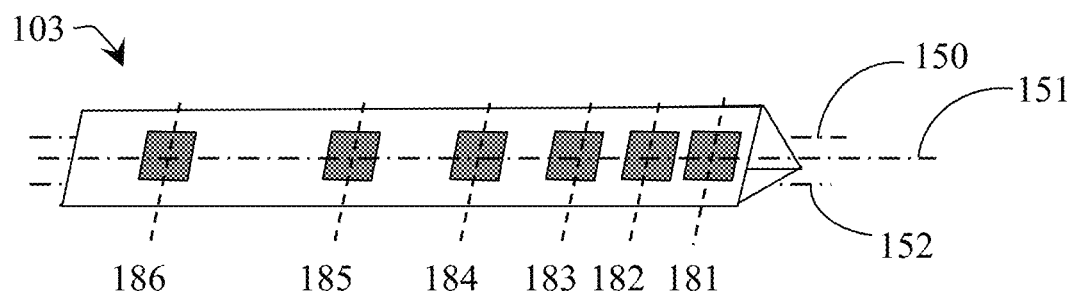
Figure 3C:
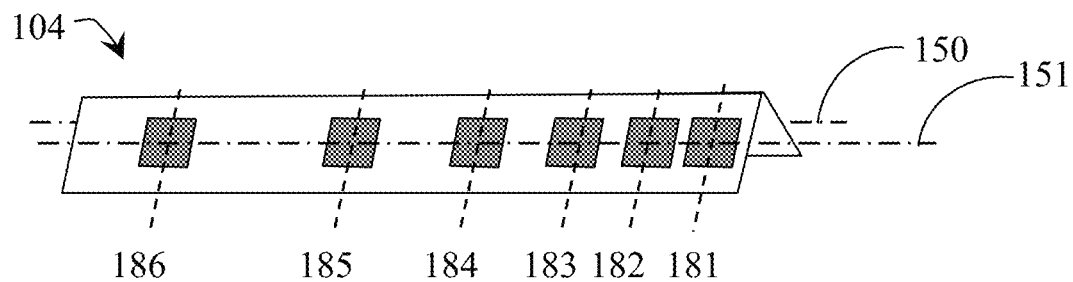

The embodiments described above comprises a substantially two-dimensional (2D) array of magnetic sensors. FIGS. 3A, 3B and 3C depict three-dimensional arrangements (3D arrays) of magnetic sensors.

FIG. 3A depicts a further embodiment 102 of the probe—for clarity, the magnetic marker 200 being localized and the skin 300 are not depicted. However, the measurement situation is analogous to the situation depicted in FIG. 1A and FIG. 2A.

The probe 102 comprises three rows of two or more magnetic sensors, the center of the packages being optionally disposed along six transverse axes 181 to 186. The transverse axes 181 to 186 are substantially perpendicular to three longitudinal probe axis 150 to 152. The sensors may be optionally disposed along these longitudinal axis 150 to 152, with each row of sensors being disposed on a separate face of longitudinally extended cube. The shape may also be described as a square or rectangular prism. The transverse cross-section of the probe 102 is a square or rectangle. The probe 102 of FIG. 3A may be formed by providing the probe 101 of FIG. 2A on a flexible substrate, and folding it between the rows of magnetic sensors.

Additionally, a further row of sensors may be disposed on the fourth face of the longitudinally-extended probe.

FIG. 3B depicts a further embodiment 103 of the probe. The probe 103 comprises three rows of two or more magnetic sensors, the center of the packages being optionally disposed along six transverse axes 181 to 186. The transverse axes 181 to 186 are substantially perpendicular to three longitudinal probe axis 150 to 152. The sensors may be optionally disposed along these longitudinal axis 150 to 152, with each row of sensors being disposed on a separate face of longitudinally-extended triangular prism. The transverse cross-section of the probe 102 is a triangle. The probe 103 of FIG. 3B may be formed by providing the probe 101 of FIG. 2A on a flexible substrate, and folding it between the rows of magnetic sensors.

The skilled person will also realize that other shapes of transverse cross-section may be used in longitudinally-extended forms, such as a circle, an oval, an ellipse irregular triangle, or a trapezoid.

FIG. 3C depicts a further embodiment 104 of the probe. The probe 103 comprises two rows of two or more magnetic sensors, the center of the packages being optionally disposed along six transverse axes 181 to 186. The transverse axes 181 to 186 are substantially perpendicular to two longitudinal probe axis 150 and 151. The sensors may be optionally disposed along these longitudinal axis 150 and 151, with each row of sensors being disposed on a separate face of longitudinally-extended wedge (or L) shape. The transverse cross-section of the probe 104 is a corner. The probe 104 of FIG. 3C may be formed by using two rows of magnetic sensors on a flexible substrate, and folding it between the rows of magnetic sensors.

The skilled person will also realize that the two faces may be bent, such that they contact each other on the inside. This provides a flat wand very suitable for marker 200 localization.

The skilled person will realize from the embodiments depicted in FIGS. 3A, 3B and 3C that a 3-dimensional sensor array may be provided by mounted sensors on a rigid PCB having the correct shape, or using a flexible substrate Note that a 3-dimensional arrangement of sensors may provide a higher degree of sensitivity in a plurality of directions.

By suitable dimensioning and/or substrate/component selection, the probe may have an approximately cylindrical shape, such as a probe, wand or pencil. If the probe is configured to be inserted through the skin or in a cavity, a small diameter may be preferred. With such procedures, lateral (or transverse) measurement may be less critical, and may even be omitted from the design by having a single row of sensors, extending along the probe longitudinal axis 150 as depicted in FIGS. 2A and 2B.

Determining the one or more dispositions of the magnetic marker 200 using the measurement data from the magnetic sensors may be performed in any suitable way. For example, three types of algorithms were evaluated:

(1) a solver which uses iteration to solve for the unknown parameters;
(2) a rangefinder which gives an indication of the distance and possibly direction of the magnetic marker 200; and
(3) differential measurement
(1) The iterative localization algorithm finds the position of the magnet by simulating the expected magnetic fields at the known sensor positions by assuming a magnet 200 (with a known dipole moment) at some position and orientation. For these marker locations and orientations, a forward 3D-model (as described above) may be provided to simulate the predicted field at each magnetic sensor. The optimization algorithm may then minimize the difference between the measured and predicted fields at the sensor. The sum of squares (least squares) may be minimized, or any other suitable approach.

It then compares the simulated magnetic fields against the measurements and, using optimization techniques, iteratively finds the set of parameters that minimizes the difference between the measurement and prediction.

The optimization may fit for 9 parameters:

Magnet position (x, y, z)

Magnet orientation (nx, ny, nz)

Background field (B0x, B0y, B0z)

The magnet orientation is a unit vector and the cost function applies this constraint internally, which means that there are 8 degrees of freedom. Optimization may use any convenient algorithm, such the Trust Region Reflective algorithm in least squares from the scipy.optimize package. This particular algorithm is reasonably efficient and allows optimization of the parameters within given bounds. Many of the conventional magnetic marker localization publications suggest the Levenberg-Marquardt algorithm, but this is less preferred because it is unbounded. When applied to the probe according to the invention, unbounded optimization occasionally gave unrealistic solutions while the bounded Trust Region Reflective algorithm gave more robust solutions.

The algorithm evaluates and returns the Jacobian, which may be used to indicate uncertainty in the estimated position. This is a modified version of the approach used to indicate uncertainty in a GPS position fix. The uncertainty provides an indication of whether the magnetic marker 200 is inferred to be inside the beam or so poorly localized that it is deemed not detected.

A position boundary of ±80 mm was assumed in all directions. The background field vector was limited to ±100 µT in each direction. The orientation of the magnetic field was constrained to ±1 in each direction, and its magnitude was constrained by the cost function to 1.

The optimization algorithm used was a gradient method and the Jacobian was calculated numerically. When the probe is stationary, the marker position inferred may jump to another location—to stabilize this, the solution from the previous sample may be fed back as the initial starting point for the next sample.

(2) The non-iterative localization algorithm (rangefinder) just infers the distance to the magnetic marker 200. The distance to the marker 200 from each sensor may be estimated from the magnitude of the magnetic field measured by each sensor, which is given by:

$$|B| = |m|\frac{\sqrt{(1+3\cos^2\theta)}}{r^3}$$

But |B| depends on the orientation of the magnet 200; θ is the angle between the magnet's pole and the vector between the magnet 200 and the sensor. This means that at a given distance r, |B| is twice as strong when the sensor is along the poles of the magnet (i.e. inclination angle θ=0 in spherical polar coordinates relative to the dipole) than when the sensor is around the 'equator of the magnet θ=90 degrees). $|B| \propto 1/r^3$ so the error in r without knowledge of θ is $1/(\sqrt[3]{2})=0.79$.

Figure 4:
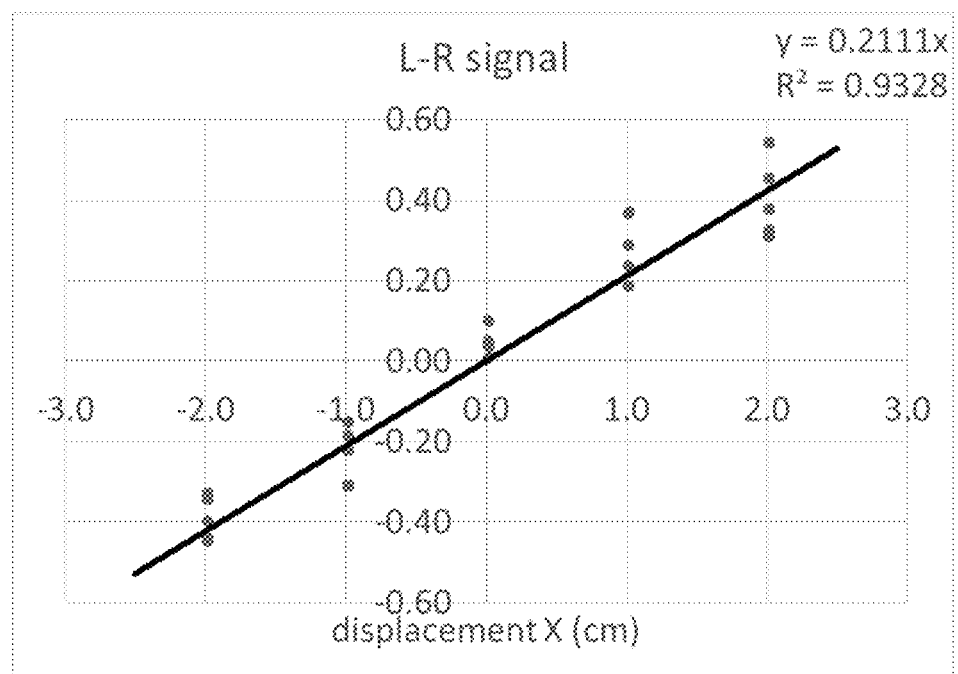
FIG. 4 depicts an example of a simple differential measurement showing the correlation between signal and marker lateral displacement.

(3) FIG. 4 depicts an example of differential measurement versus lateral displacement characteristic which may be used to convert the L-R signal from a sensor to lateral displacement. From each sensor (L and R) the magnitude of the magnetic field is measured. Differential measurements are made by comparing field strengths at neighboring sensors. For example, left versus right; front versus back, top versus bottom. If the differential is zero, the marker 200 is disposed close to the middle point between the sensors. If the differential is positive, the marker is disposed more to the right. If the differential is negative, the marker is disposed more to the left The x-axis shows displacement X in centimeters, from −3.0 to +3.0. The Y-axis shows the L-R signal from −0.60 to 0.60. Using a magnetic marker 200 which is cylindrical, made of NdFeB, 4 mm in length, and 2 mm in diameter, the L-R signal was measured at transverse dispositions of X=−2.0, −1.0, 0, +1.0 and +2.0. These distances are in the range five to twenty times a dimension of the magnetic marker 200. At X=0, the magnetic marker 200 is disposed on the probe longitudinal axis 150. Based on these values, a characteristic has been fitted, which is a straight line from −2.5, −0.52775 to 2.5, 0.52775. In other words, the distance X may be calculated from L−R=0.2111X. In this example, the correlation factor ($R^2$) of the linear curve fit is 0.9328.

For any of the approaches, it may be advantageous to filter the magnetic field measurements before the optimization. It may also be advantageous to filter the predicted dispositions.

Additionally, it may be advantageous to weigh the sensors by the Signal-to-Noise Ratio (SNR) and/or weigh sensors based on their relative positions within the probe 100. For example, give the sensors closest to the proximal end 165 a lower weighting as they may measure a weaker magnetic signal than sensors closest to the distal end 160.

Additionally, it may also be advantageous to constrain the search space by excluding magnetic marker 200 locations that are unlikely, or even impossible, such as those inside the probe.

Alternatively, an approach such as the Unscented Kalman Filter to constrain the location using previously deduced locations of the probe may be used. This is described further in Marius Birsan, "Unscented Particle Filter for Tracking a Magnetic Dipole Target", Proceedings of OCEANS 2005 MTS/IEEE (2005).

Alternatively, instead of estimating a unique location, it may be advantageous to estimate the probability distribution of the marker location, which will be a 3-dimensional region in space.

One of the insights on which the invention is based is that known probes were limited in that only a relative distance is measured, and the sensitivity is optimized for dispositions where the distal end is relatively close to the magnetic marker 200. At distances further away, the sensitivity and accuracy with conventional probes is reduced, increasing the chance of incorrect detection. By providing at least one measurement using sensors having a major sensor separation, a probe is provided with sensitivity both close to the magnetic marker 200 and further away.

The higher degree of accuracy and sensitivity allows improved guidance to be provided to the user using, for example, visual, audio or vibrational cues and/or visual information. Conventional probes use AC-susceptometry and provide no 3D guidance and no directionality, only relative proximity—the prior art systems rely on the healthcare professional guessing the position of the marker, and moving and tilting the probe to see the positions and orientations with the highest measurement value. This often results in a trial and error way of detecting the disposition of magnetic markers. Other probes use RF-ID or Electro-Magnetic, but this only provides (relative) distance, and not 3D information. Some probes use radioactive seed—this may provide a degree of direction (collimation), but no disposition information is provided as there is a low degree of signal decay with distance.

A suitable user interface may be provided to give the user guidance and cues, either comprised in the probe 100 or comprised in the magnetic detector. This may be relatively simple, for example, audio feedback to represent a longitudinal disposition 250, 255 (e.g. by modifying pitch), audio feedback to represent a transverse disposition 260. (e.g. by a continuous tone when the position of the magnetic marker 200 coincides with the probe longitudinal axis 150. A more complicated user interface may also be provided, such as a graphical representation (e.g. 2D targeting cross) indicating direction, or a graphical 3D representation showing the marker 200 and the relative location of the probe 100 (or vice-versa).

This lack of clear guidance is also the case for conventional radio-active markers, that have the additional disadvantage of safety issues in addition to lacking 3D guidance. For conventional Electro-Magnetic and RFID markers, they have the disadvantages that they must remain active, they are susceptible to failure, they are bulky in addition to lacking 3D guidance.

The magnetic marker 200 may comprise any suitable magnetic materials such as AlNiCo, SmCo, NdFeB and any combination thereof. For example: cylindrical, made of NdFeB, 4 mm in length, and 2 mm in diameter.

Preferably, magnetic markers 200 should be used with a small size and high remnant field. The probe 100 may be configured and arranged to detect the disposition of a marker 200 at several centimeters distance 250, 255, 260. The probe 100 may be dimensioned for convenient handheld use.

Such magnetic markers are almost unbreakable, and have passive material properties. They are biologically inert, making them inherently suitable for implantation. In addition, health risks and regulations are reduced when compared to radio-active markers. Also the availability and supply of radio-active markers is limited. Also, there are no active components which may fail during use, such as with Electro-Magnetic and RFID types.

MagSeed® magnetic marker 200 are advantageous to be used with the probe according to the invention—they are available in lengths less than 5 mm, which is smaller than typical lesions and tumors. They have a high magnetic susceptibility, and typically have a minimal remnant field >0.3 T of the marker's magnetic material, allowing a detection distance of several centimeters. In addition, this degree of detection is also possible against the background field of the Earth, which is typically approximately 10 uT. Conventional detectors for MagSeed® magnetic markers rely on susceptibility detection, which is limited in detection distance in addition to lacking 3D guidance.

3 mm lengths are also available—this may be used for surgical applications. With a suitably configured and arranged probe 100, the disposition of these 3 mm markers 200 after implantation may be determined at both several centimeter distance of the distal end 160 from the marker 200 (using the third and fourth magnetic sensors), and also may be determined at close (approximately) 1-2 mm distances (using the first and second magnetic sensors).

To be configured for implantation, the magnetic markers are preferably encapsulated or packaged in a biologically-safe material, such as titanium, parylene, silicone or any combination thereof.

The skilled person will realize that with a suitable translation formula or a matrix, marker 200 dispositions relative to a reference axis, such as the transverse and longitudinal axes, may be converted to dispositions relative to the probe longitudinal axis 150 and any transverse axis passing through a surface of the distal end 160 of the probe. Vice-versa conversions may also be performed where necessary.

The probe according to the invention may comprise any suitable magnetic sensor, and any suitable mix of sensors.

For example: using a magnetic marker 200 which is cylindrical, made of NdFeB, 4 mm in length, and 2 mm in diameter, the following measurement values were obtained with a probe 101 configuration as depicted in FIGS. 2A and 2B.

6. Sensor layout: as depicted in FIGS. 2A and 2B with sensors disposed along three longitudinal axes 150 to 152, and six transverse axes 181 to 186

Longitudinal array length 400: approx. 40 mm

Transverse array width 500: approx. 10 mm

Minor sensor separation in group 110: approx. 5 mm

Distance between transverse axes 181 and 182: approx. 5 mm

Distance between transverse axes 182 and 183: approx. 5 mm

Distance between transverse axes 183 and 184: approx. 7 mm

Distance between transverse axes 184 and 185: approx. 10 mm

Distance between transverse axes 185 and 186: approx. 15 mm

The distal end 160 of the probe 101 was disposed approximately 20 mm longitudinally from the magnetic marker, and disposed approximately −20 mm transversely from magnetic marker (in other words, the magnetic marker 200 was lying "below" the probe longitudinal axis 150 as depicted in FIG. 1A). The probe for these measurements comprised Melexis MLX90393 Micropower Triaxis Magnetometer sensors (see above).

| | [Marker] | | | | | |
|---|---|---|---|---|---|---|
| | 186 | 185 | 184 | 183 | 182 | 181 |
| 150 | 3.3 | 6.4 | 10.3 | 17.7 | 14.8 | 26.9 |
| 151 | | | 12.4 | 19.9 | 26.1 | 38.3 |
| 152 | 3.9 | 7.8 | 12.3 | 21.5 | 38.5 | 50.2 |

Using the same sensor layout, a similar measurement was performed with the distal end 160 of the probe 101 disposed approximately 15 mm longitudinally from the magnetic marker, and disposed approximately +10 mm transversely from magnetic marker (in other words, the magnetic marker 200 lying "above" the probe longitudinal axis 150, the opposite situation to that depicted in FIG. 1A).

| | [Marker] | | | | | |
|---|---|---|---|---|---|---|
| | 186 | 185 | 184 | 183 | 182 | 181 |
| 150 | 6.2 | 12.1 | 25.9 | 51.4 | 89.9 | 164.5 |
| 151 | | | 24.9 | 47.3 | 77.8 | 142.6 |
| 152 | 5.5 | 11.6 | 22.2 | 41.4 | 57.6 | 112.4 |

The magnetic sensor array may be mounted as a 2-dimensional array on a PCB using conventional techniques. The array may also be mounted on a flat large-dimensioned substrate if the probe is used for transcutaneous location only. For example, locating the magnetic marker 200 prior to a surgeon making an incision.

Having a large array of sensors may be advantageous as individual sensors may be selected and deselected to create a "scanning" effect. In other words, the disposition of the marker may be determined with no (or minimal) movement of the probe in transverse or longitudinal directions. With such procedures, depth (or longitudinal disposition determination) may be less critical, or may even be omitted from the design.

Additionally, the probe may comprise additional sensors to provide for measurement of the orientation of probe. For example, the pitch, roll and yaw angle of the probe from an IMU (inertial measurement unit) sensor, the orientation relative to the background magnetic field from the background field sensor or other inputs. This orientation may also be considered when determining the disposition of the magnetic marker 200.

Any other inputs that give position information may be used—for example, an optical sensor, similar to the sensor used on an optical mouse, may be used to determine a contact point on the surface of the skin.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

Note that the use of the labels first, second, third and fourth for the sensors in the claims is distinct and not necessarily the same as the labels first, second and third for the sensor groups used in the description. The first, second, third and fourth sensors may be selected from any of those groups in accordance with the functionality performed by the different embodiments.

In general, a magnetic sensor may be functionally configured and arranged to co-operate with both one or more other magnetic sensors, forming one or more magnetic sensor pairs. In some cases, it may be advantageous for a single sensor to be configured and arranged to be separated by a minor sensor separation with a further magnetic sensor, as well as configured and arranged to be separated by a major sensor separation with a still further magnetic sensor. Alternatively or additionally, the skilled person will also realize that it may be convenient to use an axial/radial co-ordinate system for two or more magnetic sensors. A plurality of axial axes may be used, each with one or more corresponding radial axes—as indicated above, the skilled person can easily convert between the different co-ordinate systems. For example, when magnetic sensors 110, 120, 130 are configured and arranged to be separated by the major sensor disposition along the probe longitudinal axis, this may be considered to be an axial axis or axial direction. This may also be considered, for example, to be a central axial axis. Any magnetic sensors 110, 120, 130 configured and arranged to be separated by a minor sensor disposition may then be considered to be disposed along a radial axis or radial direction.

REFERENCE NUMBERS USED IN DRAWINGS 0-15 a first to sixteenth magnetic sensor
100 a first embodiment of a magnetic field probe
101 a second embodiment of a magnetic field probe
102 a third embodiment of a magnetic field probe
103 a fourth embodiment of a magnetic field probe
104 a fifth embodiment of a magnetic field probe
110 first sensor group
120 second sensor group
130 third sensor group
150 a first probe longitudinal axis
151 a second longitudinal sensor axis
152 a third longitudinal sensor axis
160 a distal end of probe
165 a proximal end of probe
181 a first transverse sensor axis
182 a second transverse sensor axis
183 a third transverse sensor axis
184 a fourth transverse sensor axis
185 a fifth transverse sensor axis
186 a sixth transverse sensor axis
200 implantable magnetic marker
250 longitudinal distance below outer surface of skin (depth)
255 spacing between distal end of probe & outer surface of skin (clearance)
260 transverse disposition of magnetic marker from longitudinal axis
300 an outer surface of skin
400 longitudinal extent of the sensor array
500 transverse extent of the sensor array
601 magnetic field (T)
602 distance (mm)
610 finite element model of field along magnetic marker axis
615 finite element model of field along magnetic marker radius
620 Earth magnetic field
701 magnetic field (T)
702 distance (mm)
710 finite element model of field along magnetic marker axis
715 finite element model of field along magnetic marker radius
720 Earth magnetic field

The invention claimed is:

1. A magnetic field probe for determining a disposition of an implantable magnetic marker, the probe extending along a probe longitudinal axis, the probe comprising:
a distal end, configured and arranged to be disposed close to an outer surface of skin;
a first magnetic sensor close to the distal end;
a second magnetic sensor, close to the distal end, configured and arranged to be separated by a minor sensor separation from the first magnetic sensor, the first magnetic sensor and the second magnetic sensor being configured and arranged to determine, in use, one or more dispositions of the implantable magnetic marker; and
a third magnetic sensor close to a proximal end, configured and arranged to be separated by a major sensor separation from the second magnetic sensor, the third and second magnetic sensor being configured and arranged to further determine, in use, the one or more dispositions of the implantable magnetic marker;
wherein the major sensor separation is larger than the minor sensor separation;
wherein the first magnetic sensor and the second magnetic sensor are substantially disposed along a transverse axis, the transverse axis intersecting the probe longitudinal axis;
wherein at least one of the first magnetic sensor, the second magnetic sensor, and the third magnetic sensor are comprised in an arrangement of two or more magnetic sensors in a 1D, 2D, or 3D array;
wherein the first magnetic sensor and the second magnetic sensor are co-linear along the transverse axis, and wherein the second magnetic sensor and the third magnetic sensor are co-linear along an axis parallel to the probe longitudinal axis;
wherein the distal end of the probe is further configured and arranged to contact an outer surface of skin and/or to be inserted through an outer surface of skin and/or to be inserted into a body cavity or to be used at a distance from the skin;
wherein the probe is configured to detect the magnetic field due to the orientation of the sensors relative to the probe longitudinal axis; and
wherein a length of the probe longitudinal axis is greater than a length of the probe transverse axis.

2. The probe according to claim 1, wherein the probe further comprises a fourth magnetic sensor, close to the distal end; and
wherein the fourth magnetic sensor is configured and arranged, instead of the second magnetic sensor, to be separated from the third magnetic sensor by the major sensor separation.

3. The probe according to claim 1, wherein magnetic sensors configured and arranged to be separated by the major sensor separation, are substantially disposed along a longitudinal axis.

4. The probe according to claim 1, wherein the magnetic sensors configured and arranged to be separated by the major sensor disposition, are substantially disposed along the probe longitudinal axis.

5. The probe according to claim 1, wherein the first and second magnetic sensors are substantially disposed along the transverse axis, the transverse axis being approximately perpendicular to the probe longitudinal axis, along which sensors are configured and arranged to be separated by a major sensor separation.

6. The probe according to claim 1, wherein the at least one of the first magnetic sensor, the second magnetic sensor, and the third magnetic sensor is configured and arranged to determine one of the one or more dispositions of the implantable magnetic marker with respect to the distal end of the probe.

7. The probe according to claim 1, wherein at least one magnetic sensor is configured and arranged to determine one of the one or more dispositions of the implantable magnetic marker in more than one degree of freedom.

8. The probe according to claim 7, wherein at least one magnetic sensor is configured and arranged to determine a disposition of the implantable magnetic marker in three degrees of freedom.

9. The probe according to claim 1, wherein the probe comprises one or more compensation sensors for measuring a background magnetic field; and wherein the determination, in use, of one or more dispositions of the implantable magnetic marker further considers the background magnetic field.

10. The probe according to claim 1, wherein the minor sensor separation and/or the major sensor separation is predetermined by considering the inverse cube law determination of a magnetic field strength associated with the implantable magnetic marker.

11. The probe according to claim 1, wherein a ratio of the major sensor separation to the minor sensor separation is in the range 1.25 to 40.

12. The probe according to claim 1, wherein the ratio of the major sensor separation to the minor sensor separation is in the range of 1.6 to 7.6.

13. A detector unit for detecting the disposition of an implantable magnetic marker, the detector unit comprising the magnetic probe according to claim 1.

14. A method for determining a disposition of an implantable magnetic marker comprising:
providing a probe comprising a distal end, configured and arranged to be disposed close to an outer surface of skin, the probe extending along a probe longitudinal axis and further comprising: a first magnetic sensor close to the distal end and a second magnetic sensor, configured and arranged to be separated by a minor sensor separation from the first magnetic sensor, and a third magnetic sensor close to a proximal end, configured and arranged to be separated by a major sensor separation from the second magnetic sensor, the first and second magnetic sensor being substantially disposed along a transverse axis, the transverse axis intersecting the probe longitudinal axis, the distal end of the probe being further configured and arranged to contact an outer surface of skin and/or to be inserted through an outer surface of skin and/or to be inserted into a body cavity;
configuring and arranging the first and second magnetic sensors to determine, in use, one or more dispositions of the implantable magnetic marker;
configuring and arranging the third and second magnetic sensors to further determine, in use, the one or more dispositions of the implantable magnetic marker;
wherein at least one of the first magnetic sensor, the second magnetic sensor, and the third magnetic sensor are comprised in an arrangement of two or more magnetic sensors in a 1D, 2D, or 3D array;
wherein the first magnetic sensor and the second magnetic sensor are co-linear along the transverse axis, and wherein the second magnetic sensor and the third magnetic sensor are co-linear along an axis parallel to the probe longitudinal axis;
wherein the probe is configured to detect the magnetic field due to the orientation of the sensors relative to the probe longitudinal axis; and
wherein a length of the probe longitudinal axis is greater than a length of the probe transverse axis.

15. The method according to claim 14, wherein the probe further comprises a fourth magnetic sensor, close to the distal end; and
wherein the method comprises:
configuring and arranging the fourth magnetic sensor, instead of the second magnetic sensor, to be separated from the third magnetic sensor by the major sensor separation.

16. The method according to claim 14, wherein a ratio of the major sensor separation to the minor sensor separation is in the range 1.25 to 40.

17. The method according to claim 14, wherein the ratio of the major sensor separation to the minor sensor separation is in the range of 1.6 to 7.6.

* * * * *